US012590949B2

(12) United States Patent
Ferte et al.

(10) Patent No.: US 12,590,949 B2
(45) Date of Patent: Mar. 31, 2026

(54) RADIOMICS-BASED IMAGING TOOL TO MONITOR TUMOR-LYMPHOCYTE INFILTRATION AND OUTCOME IN CANCER PATIENTS TREATED BY ANTI-PD-1/PD-L1

(71) Applicant: Institut Gustave-Roussy, Villejuif (FR)

(72) Inventors: Charles Ferte, Bethesda, MD (US); Elaine Johanna Limkin, Cachan (FR); Roger Sun, Paris (FR); Eric Deutsch, Paris (FR)

(73) Assignees: Institut National de la Sante et de la Recherche Medicale, Paris (FR); Universite Paris-Saclay, Gif-sur-Yvette (FR)

( * ) Notice: Subject to any disclaimer, the term of this patent is extended or adjusted under 35 U.S.C. 154(b) by 1140 days.

(21) Appl. No.: 16/630,031

(22) PCT Filed: Jul. 13, 2018

(86) PCT No.: PCT/EP2018/069169
§ 371 (c)(1),
(2) Date: Jan. 10, 2020

(87) PCT Pub. No.: WO2019/012147
PCT Pub. Date: Jan. 17, 2019

(65) Prior Publication Data
US 2021/0003555 A1     Jan. 7, 2021

Related U.S. Application Data

(60) Provisional application No. 62/532,139, filed on Jul. 13, 2017.

(30) Foreign Application Priority Data

Jun. 1, 2018     (EP) .................................... 18305680

(51) Int. Cl.
G01N 33/50     (2006.01)
A61B 6/00     (2024.01)
(Continued)

(52) U.S. Cl.
CPC ....... G01N 33/5005 (2013.01); A61B 6/5217 (2013.01); G01N 33/505 (2013.01);
(Continued)

(58) Field of Classification Search
None
See application file for complete search history.

(56) References Cited

U.S. PATENT DOCUMENTS

2012/0184840 A1*     7/2012     Najarian ............... G06F 18/253
                                                          600/407
2013/0309250 A1*     11/2013     Cogswell ......... G01N 33/57492
                                                          530/388.2
(Continued)

FOREIGN PATENT DOCUMENTS

WO     2014115065 A1     7/2014
WO     2016083791 A1     6/2016

OTHER PUBLICATIONS

Aerts et al., "Decoding tumour phenotype by noninvasive imaging using a quantitative radiomics approach," Nature Communications, 5:4006, 2014.
(Continued)

*Primary Examiner* — Jonathan Cwern
(74) *Attorney, Agent, or Firm* — Rouget F. Henschel; Potomac Law Group, PLLC

(57) ABSTRACT

The present invention proposes a radiomics-based bio-marker for detecting the presence and the density of tumor infiltrating CD8 T-cells in a solid tumor without having to use any biopsy of said tumor. The invention also proposes to use this information to assess the immune phenotype of said (Continued)

Figure 1:
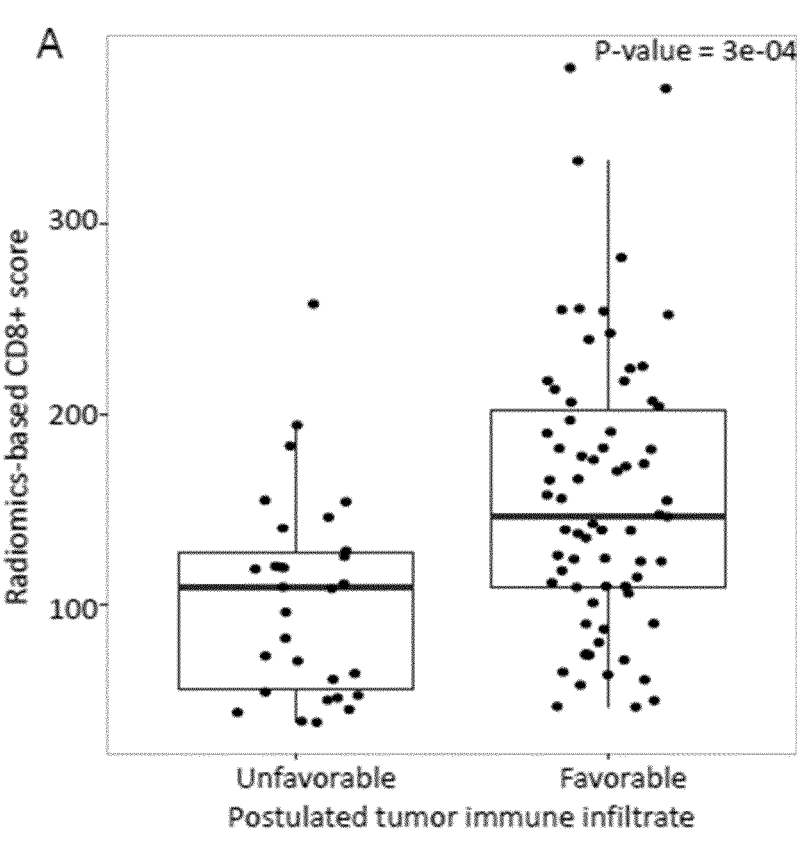
Figure 1:
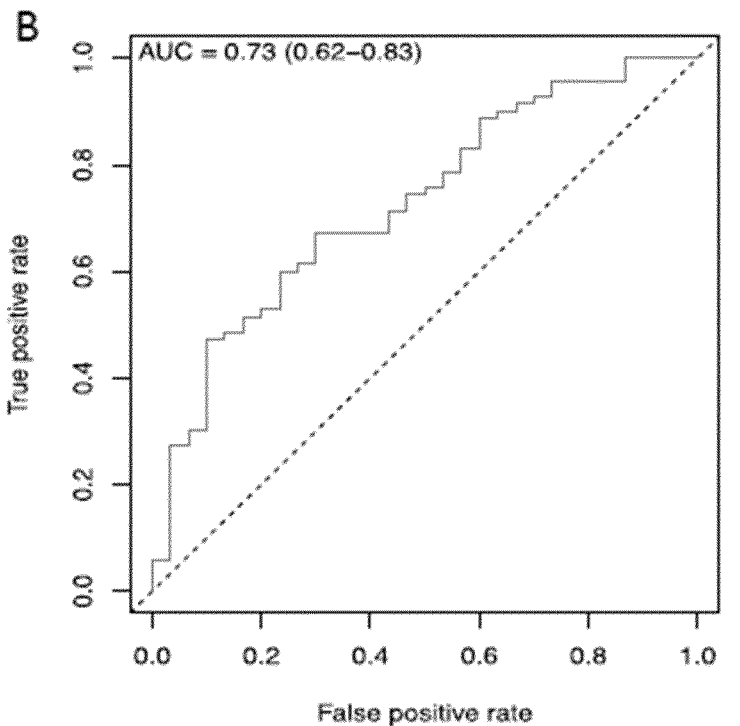

solid tumor. In a particular embodiment, the invention proposes to prognose the survival and/or the treatment efficiency of cancer patients treated with immunotherapy such as anti-PD-1/PD-L1 monotherapy.

14 Claims, 13 Drawing Sheets

(51) Int. Cl.

| | |
|---|---|
| *G01N 33/574* | (2006.01) |
| *G06T 7/00* | (2017.01) |
| *G16H 30/40* | (2018.01) |
| *G16H 50/20* | (2018.01) |

(52) U.S. Cl.

CPC .......... *G01N 33/574* (2013.01); *G06T 7/0012* (2013.01); *G16H 30/40* (2018.01); *G16H 50/20* (2018.01); *G01N 2800/52* (2013.01); *G01N 2800/7028* (2013.01)

(56) References Cited

U.S. PATENT DOCUMENTS

| | | | | |
|---|---|---|---|---|
| 2015/0356730 | A1* | 12/2015 | Grove ....................... | G06T 7/64 |
| | | | | 382/124 |
| 2016/0260211 | A1* | 9/2016 | Gillies ...................... | G06T 7/41 |
| 2017/0193175 | A1 | 7/2017 | Madabhushi et al. | |
| 2017/0352157 | A1* | 12/2017 | Madabhushi .......... | G16H 30/40 |

OTHER PUBLICATIONS

Ansell, "Hodgkin Lymphoma: Diagnosis and Treatment," Mayo Clin. Proc., vol. 90, No. 11, pp. 1574-1583, Nov. 2015.
Antonia et al. "Durvalumab after Chemoradiotherapy in Stage III Non-Small-Cell Lung Cancer," The New England Journal of Medicine, vol. 377, pp. 1919-1929, Sep. 2017.
Arkenau et al., "Prospective Validation of a Prognostic Score to Improve Patient Selection for Oncology Phase I Trials," Journal of Clinical Oncology, vol. 27, No. 16, pp. 2692-2696, Jun. 2009.
Balermpas et al., "Tumour-infiltrating lymphocytes predict response to definitive chemoradiotherapy in head and neck cancer," British Journal of Cancer, vol. 110, No. 2, pp. 501-509, Oct. 2013.
Becht et al., "Estimating the population abundance of tissue-infiltrating immune and stromal cell populations using gene expression," Genome Biology, vol. 17, p. 218, 2016.
Braman et al., "Intratumoral and peritumoral radiomics for the pretreatment prediction of pathological complete response to neoadjuvant chemotherapy based on breast DCE-MRI," Breast Cancer Research, vol. 19, No. 57, 2017.
Cataldo et al., "Mining textural knowledge in biological images: Applications, Methods and Trends," Computational and Structural Biotechnology Journal, vol. 15, pp. 56-67, 2017.
Champiat et al., "Hyperprogressive Disease is a New Pattern of Progression in Cancer Patients Treated by Anti-PD-1/PD-L1," Clinical Cancer Research, vol. 23, No. 8, pp. 1920-1928, Nov. 2018.
Chen et al., "Associations of Tumor PD-1 Ligands, Immunohistochemical Studies, and Textural Features in F-FDG PET in Squamous Cell Carcinoma of the Head and Neck," Scientific Reports, vol. 8, No. 105, Jan. 2018.
Chen et al., "Elements of cancer immunity and the cancer-immune set point," Nature, vol. 541, pp. 321-330, Jan. 2017.
Clark et al., "The Cancer Imaging Archive (TCIA): Maintaining and Operating a Public Information Repository," J. Digit Imaging, vol. 26, pp. 1045-1057, Jul. 2013.
Clemente et al., "Prognostic Value of Tumor Infiltrating Lymphocytes in the Vertical Growth Phase of Primary Cutaneous Melanoma," Cancer, vol. 77, No. 7, pp. 1303-1310, Apr. 1996.

Eisenhauer et al., "New response evaluation criteria in solid tumours: Revised RECIST guideline (version 1.1)," European Journal of Cancer, vol. 45, pp. 228-247, 2009.
Fletcher et al., "Dealing with Uncertainty in CT Images," Radiology, vol. 279, No. 1, pp. 5-10, Apr. 2016.
Gajewski et al., "Cancer immunotherapy strategies based on overcoming barriers within the tumor microenvironment," Current Opinion in Immunology, vol. 25, pp. 268-276, 2013.
Galloway et al., "Texture Analysis Using Gray Level Run Lengths," Computer Graphics and Image Processing, vol. 4, pp. 172-179, 1975.
Gandhi et al., "Pembrolizumab plus Chemotherapy in Metastatic Non-Small-Cell Lung Cancer," The New England Journal of Medicine, vol. 378, No. 22, pp. 2078-2092, May 2018.
Gillies et al., "Radiomics: Images are More than Pictures, They are Data," Radiology, vol. 278, No. 2, pp. 563-570, Feb. 2016.
Grossman et al., "Defining the biological basis of radiomic phenotypes in lung cancer," Elife, vol. 6, DOI:10.7554/eLife.23421, Jul. 2017.
Hegde et al., "The Where, the When, and the How of Immune Monitoring for Cancer Immunotherapies in the Era of Checkpoint Inhibition," Clin. Cancer Res., vol. 22, No. 8, pp. 1865-1874, Apr. 2016.
Hellmann et al., "Nivolumab plus ipilimumab as first-line treatment for advanced non-small-cell lung cancer (CheckMate 012): results of an open label, phase 1, multicohort study," Lancet Oncol., vol. 18, No. 1, pp. 31-41, Jan. 2017.
Herbst et al., "Predictive correlates of response to the anti-PD-L1 antibody MPDL3280A in cancer patients," Nature, vol. 515, No. 7528, pp. 563-567, Nov. 2014.
Hugo et al., "Genomic and Transcriptomic Features of Response to Anti-PD-1 Therapy in Metastatic Melanoma," Cell, vol. 165, No. 1, pp. 35-44, Mar. 2016.
International Search Report issued in application PCT/EP2018/069169 dated Sep. 21, 2018.
Joyce et al., "T cell exclusion, immune privilege, and the tumor microenvironment," Cancer Immunology and Immunotherapy, vol. 348, Issue 6230, pp. 74-80, Apr. 2015.
Kim et al., "Immune-escape to PD-L1/PD-1 blockade: 7 steps to success (failure)," Annals of Oncology, vol. 27, No. 8, pp. 1492-1504, May 2016.
Kuhn et al., Caret: Classification and Regression Training, pp. 1-223, Jan. 2020.
Leijenaar et al., "The effect of SUV discretization in quantitative FDG-PET Radiomics: the need for standardized methodology in tumor texture analysis," Scientific Reports, vol. 5, No. 11075, Aug. 2015.
Liaw et al., "Classification and Regression by randomForest," R News, vol. 2, No. 3, pp. 18-22, 2002.
Limkin et al., "Promises and challenges for the implementation of computational medical imaging (radiomics) in oncology," Annals of Oncology, vol. 28, pp. 1191-1206, Feb. 2017.
Massard et al., "High-Throughput Genomics and Clinical Outcome in Hard-to-Treat Advanced Cancers: Results of the MOSCATO 01 Trial," Cancer Discovery, vol. 7, No. 6, pp. 586-595, Apr. 2017.
Melero et al., "T-Cell and NK-Cell Infiltration into Solid Tumors: A Key Limiting Factor for Efficacious Cancer Immunotherapy," Cancer Discov., vol. 4, No. 5, pp. 522-526, May 2014.
Miles et al., "Colorectal Cancer: Textural Analysis of Portal Phase Hepatic CT Images as a Potential Marker of Survival," Radiology, vol. 250, No. 2, pp. 444-452, Feb. 2009.
Motzer et al., "Nivolumab versus Everolimus in Advanced Renal Cell Carcinoma," The New England Journal of Medicine, vol. 373, No. 19, pp. 1803-1813, Nov. 2015.
Nioche et al., "A freeware for tumor heterogeneity characterization in PET, SPECT, CT, MRI and US to accelerate advances in radiomics," J. Nucl. Med., vol. 58, Supplement 1, p. 1316, 2017.
Nioche et al., "LIFEx: A Freeware for Radiomic Feature Calculation in Multimodality Imaging to Accelerate Advances in the Characterization of Tumor Heterogeneity," Cancer Research, vol. 78, No. 16, pp. 4786-4789, Jun. 2018.

(56)  References Cited

OTHER PUBLICATIONS

O'Connor et al., "Imaging Intratumor Heterogeneity: Role in Therapy Response, Resistance, and Clinical Outcome," Clin Cancer Res., vol. 21, No. 2, pp. 249-257, Jan. 2015.

Ogino et al., "HLA Class I Antigen Down-regulation in Primary Laryngeal Squamous Cell Carcinoma Lesions as a Poor Prognostic Marker," Cancer Res., vol. 66, No. 18, pp. 9281-9289, Sep. 2006.

Orlhac et al., "Understanding Changes in Tumor Texture Indices in PET: A Comparison Between Visual Assessment and Index Values in Simulated and Patient Data," The Journal of Nuclear Medicine, vol. 58, No. 3, pp. 387-392, Mar. 2017.

Orooji et al., "Computerized textural analysis of lung CT to enable quantificatio of tumor infiltrating lymphocytes in NSCLC," J. Clin. Oncol., vol. 35, Suppl. 15, p. 11584, 2016.

Pages et al., "Effector Memory T Cells, Early Metastasis and Survival in Colorectal Cancer," The New England Journal of Medicine, vol. 355, No. 25, pp. 2654-2666, Dec. 2005.

Pao et al., "Tissue-Specific Immunoregulation: A Call for Better Understanding of the "Immunostat" in the Context of Cancer," Cancer Discovery, vol. 8, No. 4, pp. 395-402, Mar. 2018.

Postow et al., "Nivolumab and Ipilimumab versus Ipilimumab in Untreated Melanoma," The New England Journal of Medicine, vol. 372, No. 21, pp. 2006-2017, May 2015.

Prawira et al., "Development of a predictive radiomics signature for response to immune checkpoint inhibtors (ICIs) in patients with recurrent or matastatic squamous cell carcinoma of the head and neck," Annals of Oncology, vol. 27, Supplement 6, pp. vi328-vi350, 2016.

Reck et al., "Pembrolizumab versus Chemotherapy for PD-L1-Positive Non-Small-Cell Lung Cancer," The New England Journal of Medicine, vol. 375, No. 19, pp. 1823-1833, Nov. 2016.

Reuze et al., "Prediction of cervical cancer recurrance using textural features extracted from 18F-FDG PET images acquired with different scanners," Oncotarget, vol. 8, No. 26, pp. 43169-43179, May 2017.

Ribas et al., "PD-1 blockade expands intratumoral T memory cells," Cancer Immunol. Res., vol. 4, No. 3, pp. 194-203, Mar. 2016.

Robert et al., "Nivolumab in Previously Untreated Melanoma without BRAF Mutation," The New England Journal of Medicine, vol. 372, No. 4, pp. 320-330, Nov. 2014.

Rosenberg et al., "Atezolizumab in patients with locally advanced and metastic urothelial carcinoma who have progressed following treatment with platinum-based chemtherapy: a single arm, phase 2 trial," Lancet, vol. 387, No. 10031, pp. 1909-1920, May 2016.

Trebeschi et al., "Radiomic biomarkers for the prediction of immunotherapy outcome in patients with metastic non-small cell lung cancer," Journal of Clinical Oncology, vol. 35, Issue 15, Abstract e14520, May 2017.

Leijenaar et al., "Stability of FDG-PET Radiomics features: An integrated analysis of test-retest and interobserver variability," Acta Oncologia, vol. 52, pp. 1391-1397, 2013.

Parmar et al., "Robust Radiomics Feature Quantification Using Semiautomatic Volumetric Segmentation," PLOS One, vol. 9, No. 7, p. e102107, Jul. 2014.

Shafiq-Ul-Hassan et al., "Intrinsic dependencies of CT radiomic features on voxel size and number of gray levels," Med. Phys., vol. 44, No. 3, pp. 1050-1062, Mar. 2017.

Sun et al., "Radiomics to evaluate interlesion heterogeneity and to predict lesion response and patient outcomes using a validated signature of CD8 cells in advanced melanoma patients treated with anti-PD1 immunotherapy," J. Immunother. Cancer, vol. 10, p. e004867, 2022.

Sun et al., "Radiomics to predict outcomes and abscopal response of patients with cancer treated with immunotherapy combined with radiotherapy using a validated signature of CD8 cells," J. Immunother. Cancer, vol. 8, p. e01429, 2020.

Cohen et al., "Melanoma Brain Metastasis Pseudoprogression after Pembrolizumab Treatment," Cancer Immunol. Res., vol. 4, No. 3, pp. 179-182, Mar. 2016.

Kircher et al., "In Vivo High Resolution Three-Dimensional Imaging of Antigen-Specific Cytotoxic T-Lymphocyte Trafficking to Tumors," Cancer Research, vol. 63, pp. 6838-6846, Oct. 2003.

Obeid et al., "Heterogeneity of CD8+ tumor-infiltrating lymphocytes in non-small-cell lung cancer: impact on patient prognostic assessments and comparison of quantification by different sampling strategies," Cancer Immunol. Immunother., vol. 66, No. 1, pp. 33-43, Jan. 2017.

Pittet et al., "In vivo imaging of T cell delivery to tumors after adoptive transfer therapy," PNAS, vol. 104, No. 30, pp. 12457-12461, Jul. 2007.

Shu et al., "Quantitative PET reporter gene imaging of CD81 T cells specific for a melanoma-expressed self-antigen," International Immunology, vol. 21, No. 2, pp. 155-165, Dec. 2008.

Thompson et al., "Patterns of PD-L1 expression and CD8 T cell infiltration in gastric adenocarcinomas and associated immune stroma," Gut, vol. 66, No. 5, pp. 794-801, May 2017.

Salmon et al., "Matrix architecture defines the preferential localization and migration of T Cells into the stroma of human lung tumors," The Journal of Clinical Investigation, vol. 122, No. 3, pp. 899-910, Mar. 2012.

Sato et al., "Intraepithelial CD8+ tumor-infiltrating lymphocytes and a high CD8+/regulatory T cell ratio are associated with favorable prognosis in ovarian cancer," PNAS, vol. 102, No. 51, pp. 18538-18543, Dec. 2005.

Sun et al., "A novel radiomic based imaging tool to monitor tumor lymphocyte infiltration and outcome of patients treated by anti-PD/PD-L1," Annals of Oncology, vol. 28, Issue Suppl. 5, Sep. 2017.

Sun et al., "A radiomics approach to assess tumour-infiltrating CD8 cells and response to anti-PD-1 or anti-PD-L1 immunotherapy: an imaging biomarker, retrospective multicohort study," The Lancet Oncology, vol. 19, pp. 1180-1191, Sep. 2018.

Sun et al., "Baseline lymphopenia should not be used as exclusion criteria in early clinical trials investigating immune checkpoint blockers (PD-1/PD-L1 inhibitors)," European Journal of Cancer, vol. 84, pp. 202-211, Aug. 2017.

Sun et al., "The Radiomic Target Volume in Regard to Mattonen et al.," International Journal of Radiation Oncology, vol. 95, No. 5, pp. 1544-1548, 2016.

Takaaki et al., "Predictive relevance of PD-L1 expression combined with CD8+ TIL density in stage III non-small cell lung cancer patients receiving concurrent chemoradiotherapy," European Journal of Cancer, vol. 55, pp. 7-14, Jan. 2016.

Tang et al., "Development of an Immune-Pathology Informed Radiomics Model for Non-Small Cell Lung Cancer," Scientific Reports, vol. 8, No. 1922, Jan. 2018.

Tang et al., "Pathology-Based Non-Small Cell Lung Cancer Radiomics Signature Describing the Local Tumor Immune Environment: Discovery and Validation," International Journal of Radiation Oncology, vol. 96, No. 2, pp. 542-543, 2016.

Tumeh et al., "PD-1 blockade induces responses by inhibiting adaptive immune resistance," Nature, vol. 515, No. 7528, pp. 568-571, Nov. 2014.

Wansom et al., "Infiltrating Lymphocytes and Human Papillomavirus-16 Associated Oropharynx Cancer," Laryngoscope, vol. 122, No. 1, pp. 121-127, Jan. 2012.

Weber et al., "Safety, Efficacy, and Biomarkders of Nivolumab With Vaccine in Ipilimumab-Refractory or -Naive Melanoma," Journal of Clinical Oncology, vol. 31, No. 34, pp. 4311-4318, Dec. 2019.

Weinstein et al., "The Cancer Genome Atlas Pan-Cancer Analysis Project," Nat. Genet., vol. 45, No. 10, pp. 1113-1120, Oct. 2013.

Wen et al., "Radiomic CT Features for Evaluation of PD-L1, CD8_TILs and Foxp3+TILs Expression Status in Patients with Stage I NSCLC," International Journal of Radiation Oncology, vol. 99, Issue 2, p. E738, Oct. 2017.

Zou et al., "Regularization and variable selection via the elastic net," J.R. Statist. Soc. B, vol. 67, Part 2, pp. 301-320, 2005.

* cited by examiner

A

Spearman's r = 0.559
P-value = 0.00022

B

RADIOMICS-BASED IMAGING TOOL TO MONITOR TUMOR-LYMPHOCYTE INFILTRATION AND OUTCOME IN CANCER PATIENTS TREATED BY ANTI-PD-1/PD-L1

SUMMARY OF THE INVENTION

The present invention proposes a radiomics-based bio-marker for detecting the presence and the density of tumor infiltrating CD8 T-cells in a solid tumor without having to use any biopsy of said tumor. The invention also proposes to use this information to assess the immune phenotype of said solid tumor. In a particular embodiment, the invention proposes to predict the survival and/or the treatment effi-ciency of cancer patients treated with immunotherapy such as anti-PD-1/PD-L1 monotherapy.

BACKGROUND OF THE INVENTION

Medical image processing and analysis (also known as Radiomics) is a promising and rapidly growing discipline [1]. While the classical analysis of medical images such as computed tomography scans (CT), magnetic resonance imaging (MRI) or PET (Positron Emission Tomography) is based on the visual interpretation of simple features such as tumor size and tumor global shape, this new approach analyzes and translates images computationally into quan-titative complex data. These high dimensional data allow more in-depth characterization of the tumor phenotype [1-3], with the underlying assumption that imaging reflects not only tissue architecture but also cellular and molecular composition. The end goal of radiomics is to generate imaging biomarkers to serve as clinical decision support tools and to permit better understanding of cancer biology [4-6]. Radiomics has several advantages: (i) non-invasive, (ii) evaluates the tumor and its microenvironment in their entirety, thus characterizing spatial heterogeneity, and (iii) can be repeated over time, allowing the assessment of the changes throughout the evolution of the disease.

The arrival of immunotherapy has profoundly changed the management of multiple cancers such as melanomas [7, 8], lymphomas [9], lung [10] and renal cancers [11], with astonishing results: 10 to 40% objective tumor responses in patients with advanced stages, all tumor types combined, and up to 60% for melanomas [12-14].

Unfortunately, only 20-30% of patients respond to immu-notherapy such as anti-PD-1/PD-L1 monotherapy [12]. Sev-eral studies showed that pre-existing tumoral and peri-tumoral immune infiltration correlates with patients' responses to anti-PD-L1/PD-1 [12, 15, 16, 17]. Three dis-tinct immune phenotypes have been described: immune-inflamed, immune-excluded and immune-desert. Immune-inflamed tumors present a dense functional CD8 T-cell infiltration (TIL) reflected by increased IFNγ signaling, an expression of checkpoint markers (e.g. PD-L1), and high mutational burden. These tumors tend to respond to immu-notherapy [12, 13, 15]. Yet, in immune-excluded tumors, a variety of biological signals (TGF-beta signaling, myeloid-derived suppressor cells, angiogenesis, etc.) prevent T-cell infiltration into the tumor. The immune-desert phenotype exhibits limited infiltration of CD8 T-cells, with highly proliferating tumor cells, and the immunotherapeutic treat-ments are often vain. While immunotherapy is being increasingly used in oncology, of note, the last two random-ized trials showed that PD-L1 was not associated with response to immunotherapy [55, 56].

Hence, there is a need for the development of tools to identify patients most likely to respond to immunotherapy and thus aid patient selection and avoid unwarranted expense and toxicities for non-responders. This tool should be reliable, easy to implement, and non-invasive so as to be reproduced as frequently as possible.

Medical images possess valuable information which can be harnessed through computer assisted interpretation. This technique, termed radiomics, is a rapidly-emerging disci-pline with the goal of extracting quantitative data from medical images to be used as clinical decision support tools. In the context of oncology, information obtained from standard imaging modalities [computed tomography scan (CT), magnetic resonance imaging (MRI), and Positron emission tomography scan (PET)], usually refers to simple traits such as gross shape, contrast enhancement, and size. However, imaging information is much richer, and the goal of radiomics is to extract high throughput quantitative features, covering the fields of texture, advanced shape modeling, and heterogeneity, to name a few. The increasing resolution quality has led to three-dimensional (3D) image acquisitions containing millions of voxels available for analysis, making the development of radiomics a natural progression, as more data necessitated increased computing capabilities to harness more information.

Radiomics has immense potential to improve knowledge in tumor biology and guide the management of patients at bedside. Medical image analysis allows tumor monitoring across time, with images being routinely acquired through-out the course of treatment. Thus, imaging biomarkers may be used for and contribute to cancer detection, diagnosis, choice of therapeutic strategy, prognosis inference, predic-tion of response, and surveillance.

Four published studies have evaluated imaging as a biomarker for immune infiltration or immune pathways [54, 59-61], but no patients were treated with immunotherapy, and only one validated their radiomic-signatures in an independent cohort [60]. Grossmann et al. analyzed two independent cohorts of 262 and 89 lung cancer patients who underwent surgery to determine associations between radiomics and underlying molecular pathways [60]. Using biclustering, they identified three clusters of 58, 8, and 32 radiomic features associated with respectively 5, 30 and 27 pathways related to immune system/p53 (AUCs 0.64-0.69 in the validation set). They performed immunohistochemical staining for CD3 on 22 tumors predicted to have high or low immune response according to one radiomic feature and found agreement between radiomics and pathology (one-sided Wilcoxon test, p=0.008). However, as the choice of the radiomic feature was made according to a gene signature that was not part of the three identified radiomics-immune pathways clusters and had no proper validation, results should be interpreted with caution. Tang et al. used unsu-pervised machine learning to identify a radiomic-signature based on four features in lung cancer patients who under-went surgery [59]. This signature separated patients into four clusters (A-D). These clusters were associated with OS in the training (5-year OS: 61%, 41%, 50% and 91% for A-D, respectively, P-value=0.04) and validation sets (5-year OS: 55%, 72%, 75%, and 86% for A-D, respectively, P-value=0.002). Interestingly, cluster D had the lowest PD-L1+ tumor cell and the highest infiltrating CD3 T-cell counts. These studies showed associations between radiomics and either genomics or biology. However, the level of evidence of these studies was low, with only one study having an external validation cohort.

The present inventors postulated that radiomics could allow a reliable evaluation of tumor immune infiltration and thus lead to the identification of novel predictors of efficacy of immunotherapy.

To date, there are no published studies proposing the use of radiomics to predict specifically a patient response to immunotherapy such as anti-PD-1/PD-L1 monotherapy. The present study is the first introducing a radiomic-based biomarker for detecting tumor infiltrating CD8 T-cells which shows a reproducible and significant correlation with pathologic quantification of tumor infiltrating lymphocytes (CD8+ tumor infiltrating T cells), tumor immune phenotype and clinical responses to anti-PD-1/PD-L1 in three independent validation cohorts.

The present study is unique in that it reveals the link between standard medical images and gene expression signature of CD8 T-cells, pathologic quantification of TIL, tumor immune phenotype, and patient outcomes, especially when treated with immunotherapy. It confirms that radiomics could be an efficient, non-invasive, cost-effective and repeatable way to evaluate patients for precision medicine. The biomarker of the invention can be obtained easily given the widespread availability and routine utilization of tomography scans (CTs).

DETAILED DESCRIPTION OF THE INVENTION

Radiomics consists of the analysis of quantitative data extracted from standard medical imaging to generate imaging biomarkers. The process of radiomics consists of discrete steps: image acquisition and segmentation, feature extraction, and statistical learning. A considerable number of features can be used to assess the characteristics of a target zone.

Features may be classified into several categories. There are quantitatively extracted descriptors of size, shape, and other radiologic terminologies which characterize the tumor surface. First-order statistics are used to study the distribution of voxel values without considering spatial relationships; second-order statistics characterize spatial relationships between voxels, such as the co-occurrence matrix (GLCM), gray-level run length matrix (GLRLM), gray-level size zone matrix (GLZLM), and the neighborhood gray-level different matrix (NGLDM). Filter grids such as Gabor and Fourier may be used both in the pre-processing step and for extracting spatial or spatio-temporal features. A limitation is that some extracted values are dependent on the ROIs contoured.

The extracted features can be global (one value for the whole ROI), or local (a value per image patch) when inhomogeneous patterns are present in the image, where dimensionality significantly increases if simple concatenation of local descriptors is carried out. For this, more advanced frameworks explore compact statistical representations based on coding structures/dictionaries. A more detailed review on texture analysis methods focusing on microscopy images of cells or tissues can be found in [46].

Radiomic features in CT imagery cannot be accessed or extracted by pencil and paper or acquired by the human mind. Radiomic features present in CT imagery are sub-visual features that are not visible to the human eye.

Some of the mainly used features are disclosed in Table 1:

TABLE 1

| Matrix | Index |
|---|---|
| Conventional Indices | Min Value |
| | Mean Value |
| | Std Value |
| | Max Value |
| Histogram | Skewness |
| | Kurtosis |
| | Entropy |
| | Energy |
| Shape | Volume (ml) |
| Gray-Level | Homogeneity |
| Co-occurrence Matrix | Energy |
| | Contrast |
| | Correlation |
| | Entropy |
| | Dissimilarity |
| Gray-Level Run | SRE |
| Length Matrix | LRE |
| | LGRE |
| | HGRE |
| | SRLGE |
| | SRHGE |
| | LRLGE |
| | LRHGE |
| | GLNUr |
| | RLNU |
| | RP |
| Neighborhood | Coarseness |
| Gray-Level Difference Matrix | ContrastN |
| Gray-Level Zone Length Matrix | SZE |
| | LZE |
| | LGZE |
| | HGZE |
| | SZLGE |
| | SZHGE |
| | LZLGE |
| | LZHGE |
| | GLNUz |
| | ZLNU |
| | ZP |

Std: Standard deviation; SRE: short-run emphasis; LRE: long-run emphasis; LGRE: low gray-level run emphasis; HGRE: high gray-level run emphasis; SRLGE: short-run low gray-level emphasis; SRHGE: short-run high gray-level emphasis; LRLGE: long-run low gray-level emphasis; LRHGE: long-run high gray-level emphasis; GLNUr: gray-level non-uniformity for run; RLNU: run-length non-uniformity; RP: run percentage; SZE: short-zone emphasis; LZE: long-zone emphasis; LGZE: low gray-level zone emphasis; HGZE: high gray-level zone emphasis; SZLGE: short-zone low gray-level emphasis; SZHGE: short-zone high gray-level emphasis; LZLGE: long-zone low gray-level emphasis; LZHGE: long-zone high gray-level emphasis; GLNUz: gray-level nonuniformity for zone; ZLNU: zone length non-uniformity; ZP: zone percentage.

The Table 1 presents a selection of some radiomic features that can be extracted from images. First-order features correspond to conventional indices and features extracted from the intensity histogram. Second-order or textural features can be also extracted from four textural matrices calculated using the LIFEx software (http://www.lifexsoft-.org): the Gray-Level Co-occurrence Matrix (GLCM), the Gray-Level Run Length Matrix (GLRLM), the Neighborhood Gray-Level Difference Matrix (NGLDM) and the Gray-Level Zone Length Matrix (GLZLM). GLCM and GLRLM can be computed in 13 directions to account for all independent directions between one voxel and its 26 neighbors.

Based on some of these features, the present inventors developed a radiomics-based predictor of the presence of TILs and investigated whether such signature could predict the outcome of patients treated by anti-PD1/PDL1.

The radiomics-based predictor could contain other technical variables which are related to the CT scan such as acquisition marker e.g. kV (kilovoltage peak) or localization markers e.g. VOI (location of the volume of interest) in order to improve the reproducibility of the signature.

In a first study (cf. example 1), a first radiomics-based CD8+ signature was developed using the six radiomics features which had highest performance on random forest. Radiomics features were extracted from CT scans after manual segmentation of tumors on contrast-enhanced CTs of 57 HNSCC patients from the TCGA (The Cancer Genome Atlas)/TCIA (The Cancer Imaging Archive) databases. A predictive model of tumor infiltrating CD8+ T cells was developed with the radiomics features and RNA-Seq data using random forest. CD8+ T cells were estimated by the Microenvironment Cell Populations-counter signature. As a first validation, this classifier was applied to an independent cohort of 100 patients for which the pathologic tumor immune infiltrate was postulated as either favorable (lymphoma, melanoma, lung, bladder, renal, MSI+ cancers, and adenopathy; 70 patients) or unfavorable (adenoid cystic carcinoma, low-grade neuroendocrine tumors, uterine leiomyosarcoma; 30 patients). Second, the predictor was applied on a second external cohort of 139 patients prospectively enrolled in anti PD-1/PD-L1 phase 1 trials to infer its relation with patient outcome (overall survival (OS)). The median of the radiomics-based CD8+ score was used to separate patients into two groups. In the first external cohort, this signature was associated with the postulated tumor immune infiltrate (Wilcoxon test, P<0.001). In the second external cohort, patients with high-predicted CD8+ score had significantly better OS (HR=0.55, 95% CI=0.36-0.86, P=0.009). The radiomics-based CD8+ predicted score remained significant in a multivariate cox regression analysis including RMH score (HR=0.50, 95% CI=0.32-0.78, P=0.003).

In a second study (cf. example 2), a second radiomics-signature of tumor immune infiltration was developed from CT-scans. Access to both RNA-seq data and images of the biopsied lesion in the MOSCATO trial and clinical data of patients from anti-PD-1/PD-L1 phase 1 trials were used to assess links between imaging features, transcriptomic data, tumor immune phenotype and clinical responses to immunotherapy. Immune infiltration was still modeled using the Microenvironment Cell Populations-counter signature, and especially the CD8B gene according to the "CD8 T-cells" signature by Becht et al ([37]) which associated specifically this gene with the infiltration of CD8 T-cells and was distinct from both the "Cytotoxic T-cells" signature (which encompasses NK cells), and the "T-cells" signature (which encompasses CD4 and naive T-cells) present in the same R-package ([37]). Extraction of radiomic features from the tumor and its periphery incorporated information on both the tumor and its microenvironment [19]. The radiomic-signature of CD8 T-cells was validated in the TCGA dataset, the association with immune-phenotype was confirmed in a second independent cohort, and clinical outcomes of patients treated with anti-PD-1/PD-L1 were predicted.

Hence, the two identified by the inventors have been validated with several external and independent cohorts and can be reliably used on other cohorts. They appear as a promising tool to estimate tumor immune infiltrates in solid tumors. They can also be used to infer the outcome of patients suffering from cancer, especially those that are treated with immunotherapeutic treatments such as anti-PD1/PD-L1.

In a first aspect, the present invention relates to the use of a radiomics-based signature for evaluating the quantity and/or spatial density and/or heterogeneity and/or changes over time of tumor immune infiltrates in a solid tumor.

The term "tumor immune infiltrate" is herein synonymous of "tumor-infiltrating immune cells". These terms encompass white blood cells that have left the bloodstream and that have migrated into the tumor. These white blood cells include T cells and B cells, and also natural killer cells, macrophages, neutrophils, dendritic cells, mast cells, eosinophils, basophils, etc., that can be present in the tumors in variable proportions. Preferably, the "tumor immune infiltrate" detected by the signature of the invention is composed of tumor infiltrating lymphocytes (TILs), and, more preferably, of CD8+ tumor infiltrating lymphocytes.

In a preferred embodiment, the radiomics-based signature of the invention is used for evaluating the spatial distribution of CD8+ T cells infiltrating the tumors.

By "solid tumor", it is herein meant any kind of solid tumor, in particular of epithelial, neuroectodermal or mesenchymal origin. It can be a metastatic cancer or not. The tumor can for example be selected from, without being limited to, the group consisting of squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, brain cancer, central nervous system cancer, pancreatic cancer, glioblastoma multiforme, cervical cancer, stomach cancer, bladder cancer, malignant hepatoma, breast cancer, colon carcinoma, head and neck cancer, gastric cancer, germ cell tumor, pediatric sarcoma, rhabdomyosarcoma, Ewing's sarcoma, osteosarcoma, soft tissue sarcoma, sinonasal NK/T-cell lymphoma, myeloma, melanoma, multiple myeloma. Benign solid tumors such as uterine leiomyosarcoma are also encompassed.

In a preferred embodiment, the radiomics-based signature of the invention is used for evaluating the spatial heterogeneity and/or changes over time of tumor immune infiltrates in carcinoma, and in particular in a head and neck squamous cell carcinoma.

A CT scan, also known as computed tomography scan, makes use of computer-processed combinations of many X-ray measurements taken from different angles to produce cross-sectional (tomographic) images (virtual "slices") of specific areas of a scanned object, allowing the user to see inside the object without cutting. Other terms include computed axial tomography (CAT scan) and computer aided tomography.

Digital geometry processing is used to further generate a three-dimensional volume of the inside of the object from a large series of two-dimensional radiographic images taken around a single axis of rotation.

The term "computed tomography" (CT) is often used to refer to X-ray CT, because it is the most commonly known form. But, many other types of CT exist, such as positron emission tomography (PET) and single-photon emission computed tomography (SPECT). X-ray tomography, a predecessor of CT, is one form of radiography, along with many other forms of tomographic and non-tomographic radiography.

The radiomics-based signature of the invention is generated by non-invasive imagining technologies such as scanners, magnetic resonance imaging (MRI) or PET (Positron Emission Tomography).

In a preferred embodiment, the signature of the invention is generated from images taken by a CT scan.

The radiomics signature of the invention contains at least six (6) radiomics features or variables, preferably at least seven (7), or eight (8) radiomic features, that can be chosen in any of the matrix categories highlighted in Table 1. In a preferred embodiment, the signature of the invention combines radiomics features of at least two, and more preferably three categories.

In a preferred embodiment, the signature of the invention contains at least one, preferably two, more preferably three, even more preferably four feature(s) of the Gray-level Run Length Matrix (GLRLM) variables. These features can be combined with conventional indices such as min Values.

In a more preferred embodiment, the signature of the invention contains at least one acquisition marker, for example kVp (kilovoltage peak). This particular marker takes into account the image acquisition variability when image acquisition protocols are heterogenous, and therefore enables to use the signature on CT images from different machine and/or acquired using different image acquisition protocols, as shown in example 2 below.

In another preferred embodiment, the signature of the invention contains at least one localization marker, for example a VOI feature (location of the volume of interest) as proposed in example 2 below. Particularly preferred are the VOI markers of adenopathy and head-and-neck. It may happen that the values of these VOI markers are null when the target tumors are not from adenopathy or head-and-neck.

In another preferred embodiment, the signature of the invention contains at least one, preferably two, more preferably three Gray-Level Co-occurrence Matrix features, for example EnergyH, correlation, and/or Contrast. These parameters are preferably detected for the tumor ROI, as disclosed in example 1 (tum).

In another preferred embodiment, the signature of the invention contains features characterizing the peripheral zone of the tumor (ring) and the inside tumor (tum). Conventional indices such as maxValue can be used to characterize these zones, as disclosed in example 1.

It is also preferred to combine these markers with at least one Gray-Level Zone Length Matrix feature such as Short-Zone high gray level emphasis (SZHGE), as disclosed in example 1.

The radiomics-based signature of the invention can be used to predict the outcome of cancer patients. In a preferred embodiment, it is used to aid the skilled cancerologist in the selection of appropriate treatments for maximizing the survival of the patients. Appropriate treatments are for example chemotherapeutic treatments, immunotherapeutic treatments, radiotherapeutic treatments and/or surgery. Preferably, the signature of the invention is generated before initiating a treatment.

Specifically, said patients have been treated or will be treated with anti-cancer drugs.

Said anti-cancer agent can be selected from chemotherapy, immunotherapy (or immune checkpoint blocker), anti-cancer vaccine, radiotherapy, and surgery.

Said "chemotherapeutic agent" is typically an agent selected for example from an antitumor/cytotoxic antibiotic, an alkylating agent, an antimetabolite, a topoisomerase inhibitor, a mitotic inhibitor, a platin based component, a specific kinase inhibitor, an hormone, a cytokine, an anti-angiogenic agent, an antibody, a DNA methyltransferase inhibitor and a vascular disrupting agent.

Said antitumor agent or cytotoxic antibiotic can for example be selected from an anthracycline (e.g. doxorubicin, daunorubicin, adriamycine, idarubicin, epirubicin, mitoxantrone, valrubicin), actinomycin, bleomycin, mitomycin C, plicamycin and hydroxyurea.

Said alkylating agent can for example be selected from mechlorethamine, cyclophosphamide, melphalan, chlorambucil, ifosfamide, temozolomide busulfan, N-Nitroso-N-methylurea (MNU), carmustine (BCNU), lomustine (CCNU), semustine (MeCCNU), fotemustine, streptozotocin, dacarbazine, mitozolomide, thiotepa, mytomycin, diaziquone (AZQ), procarbazine, hexamethylmelamine and uramustine.

Said antimetabolite can for example be selected from a pyrimidine analogue (e.g. a fluoropyrimidine analog, 5-fluorouracil (5-FU), floxuridine (FUDR), cytosine arabinoside (Cytarabine), Gemcitabine (Gemzar®), capecitabine); a purine analogue (e.g. azathioprine, mercaptopurine, thioguanine, fludarabine, pentostatin, cladribine, clofarabine); a folic acid analogue (e.g. methotrexate, folic acid, pemetrexed, aminopterin, raltitrexed, trimethoprim, pyrimethamine).

Said topoisomerase inhibitor can for example be selected from camptothecin, irinotecan, topotecan, amsacrine, etoposide, etoposide phosphate and teniposide.

Said mitotic inhibitor can for example be selected from a taxane [paclitaxel (PG-paclitaxel and DHA-paclitaxel) (Taxol®), docetaxel (Taxotere®), larotaxel, cabazitaxel, ortataxel, tesetaxel, or taxoprexin]; a spindle poison or a vinca alkaloid (e.g. vincristine, vinblastine, vinorelbine, vindesine or vinflunine); mebendazole; and colchicine.

Said platin based component can for example be selected from platinum, cisplatin, carboplatin, nedaplatin, oxaliplatin, satraplatin and triplatin tetranitrate.

Said specific kinase inhibitor can for example be selected from a BRAF kinase inhibitor such as vemurafenib; a MAPK inhibitor (such as dabrafenib); a MEK inhibitor (such as trametinib); and a tyrosine kinase inhibitor such as imatinib, gefitinib, erlotinib, sunitinib or carbozantinib.

Tamoxifen, an anti-aromatase, or an anti-estrogen drug can also typically be used in the context of hormonotherapy.

A cytokine usable in the context of an immunotherapy can be selected for example from IL-2 (Interleukine-2), IL-11 (Interleukine-11), IFN (Interferon) alpha (IFNa), and Granulocyte-macrophage colony-stimulating factor (GM-CSF).

Said anti-angiogenic agent can be selected for example from bevacizumab, sorafenib, sunitinib, pazopanib and everolimus.

Said antibody, in particular the monoclonal antibody (mAb) can be selected from a anti-CD20 antibody (anti-pan B-Cell antigen), anti-Her2/Neu (Human Epidermal Growth Factor Receptor-2/NEU) antibody; an antibody targeting cancer cell surface (such as rituximab and alemtuzumab); a antibody targeting growth factor (such as bevacizumab, cetuximab, panitumumab and trastuzumab); a agonistic antibody (such as anti-ICOS mAb, anti-OX40 mAb, anti-41BB mAb); and an immunoconjugate (such as 90Y-ibritumomab tiuxetan, 131I-tositumomab, or ado-trastuzumab emtansine).

Said DNA methyltransferase inhibitor can for example be selected from 2'-deoxy-5-azacytidine (DAC), 5-azacytidine, 5-aza-2'-deoxycytidine, 1-[beta]-D-arabinofuranosyl-5-azacytosine and dihydro-5-azacytidine.

Said vascular disrupting agent can for example be selected from a flavone acetic acid derivative, 5,6-dimethylxanthenone-4-acetic acid (DMXAA) and flavone acetic acid (FAA).

Other chemotherapeutic drugs include a proteasome inhibitor (such as bortezomib), a DNA strand break compound (such as tirapazamine), an inhibitor of both thioredoxin reductase and ribonucleotide reductase (such as xcytrin), and an enhancer of the ThI immune response (such as thymalfasin).

Said immune checkpoint blocker is typically an antibody targeting an immune checkpoint. Such an immune checkpoint blocker can be advantageously selected from anti-CTLA4 (ipilimumab and Tremelimumab), anti-PD-1 (Nivolumab and Pembrolizumab), anti-PD-L1 (Atezolizumab, Durvalumab, and Avelumab), anti-PD-L2 and anti-Tim3.

Said cancer vaccine can for example be selected from a vaccine composition comprising (antigenic) peptides; a Human papillomavirus (HPV) vaccine (such as Gardasil®, Gardasil9®, and Cervarix®); a vaccine stimulating an immune response to prostatic acid phosphatase (PAP) sipuleucel-T (Provenge®); an oncolytic virus and talimogene laherparepvec (T-VEC or Imlygic®).

The radiotherapy typically involves rays selected from X-rays ("XR"), gamma rays and/or UVC rays.

The treatment which can include several anticancer agents is selected by the cancerologist depending on the specific cancer to be prevented or treated.

Specifically, said patients have been treated or will be treated with immunotherapy drugs such as anti-PD-1 and/or anti-PD-L1 drugs.

The present invention also encompasses a method for evaluating the spatial heterogeneity and/or changes over time of said tumor immune infiltrates in a solid tumor, said method comprising the steps of:

a) obtaining a radiological image of a region of a tumoral tissue, said image including a plurality of voxels;

b) specifying a region of interest (ROI) in the image;

c) extracting a set of at least 6, preferably at least 7, more preferable 8 radiomics features from said ROI;

d) calculating a score from said at least 6, preferably at least 7, more preferable 8 radiomics features;

e) comparing said score to a reference value;

f) concluding from said comparison that the tumor immune infiltrate is present or determining its density or its evolution.

The radiological image includes a set of morphological features acquired using an imaging system, such as a CT system. Accessing the radiological image may include retrieving electronic data from a computer memory, receiving a computer file over a computer network, or other computer or electronic based action.

In other terms, the invention is also drawn to an in vitro method for evaluating the density, spatial heterogeneity and/or changes over time of a tumor immune infiltrate in a solid tumor, said method comprising the steps of:

a) specifying a region of interest (ROI) in a radiological image of a region of a tumoral tissue, said image including a plurality of voxels;

b) extracting a set of at least 6, preferably at least 7, more preferable 8 radiomics features from said ROI;

c) calculating a score from said at least 6, preferably at least 7, more preferable 8 radiomics features;

d) comparing said score to a reference value;

e) concluding from said comparison that the tumor immune infiltrate is present or determining its density or its evolution.

The nature of the radiomics feature have been described above for the signature of the invention. All of them, especially the preferred ones, can be used in the methods of the invention.

The region of tumoral tissue can be either located inside the tumor, or at the periphery of said tumor (for the determination of the "ring" variable). The ROI may be annotated by an expert radiologist using a 3D slicer approach or may be annotated using an automated segmentation approach. Other annotation or segmentation approaches or techniques may be employed.

The calculated score is a continuous and linear value reflecting the density of the tumor immune infiltrate in the ROI of the analyzed solid tumor. It is calculated by computing the levels of the at least 6 radiomics features with predefined coefficients, and by summing all the computed values (see examples below).

The higher the score is, the denser the tumor immune infiltrate is likely to be. Consequently, the higher the score is, the more efficient an anti-tumoral treatment (such as immunotherapy) will be.

As used herein, the term "reference value" is a predetermined value that has been selected on a population having a defined diagnostic and prognostic of cancer. For example, it has been obtained from a population of patients responding efficiently to a define treatment (in this case, the reference value will be high). By contrast, it can be obtained from a population of patients poorly responding to a define treatment (in this case, the reference value will be low).

The reference value is preferably determined by training the machine learning classifier with images issued from particular tumors. First testing images include images of a region of a tumor that responded to immunotherapy. Second testing images include images of a region of a tumor that did not respond to immunotherapy. Accessing the testing images may include retrieving electronic data from a computer memory, receiving a computer file over a computer network, or other computer or electronic based action.

An "efficient response to a treatment" is usually concluded when the overall survival (OS) of the patient treated with said treatment is of at least one year, preferably two years, more preferably five years. Patients having such OS is also called a "responder".

Response to a treatment is more preferably defined according to RECIST 1.1 criteria [62]. A Complete Response (CR) is defined as a disappearance of all target lesions. Any pathological lymph nodes (whether target or non-target) must have reduction in short axis to <10 mm. A Partial Response (PR) is defined as at least a 30% decrease in the sum of diameters of target lesions, taking as reference the baseline sum diameters. A Progressive Disease (PD) is defined as at least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm. (Note: the appearance of one or more new lesions is also considered progression). A Stable Disease (SD) is defined as neither sufficient shrinkage to qualify for PR nor sufficient increase to qualify for PD, taking as reference the smallest sum diameters while on study.

Time of the evaluation often depends of the disease (it is usually comprised between 6 weeks and 3-6 months).

A "non-responder" is considered as a patient with a progression disease or a stable disease as defined according to RECIST 1.1 criteria.

The reference value used in the method of the invention is preferably a cut-off obtained from a specific cohort of patients (see in the examples below). It can be determined from the area under the receiver operating characteristic curve (AUC) that describes the relationship between the sensitivity and the complement of the specificity for each possible value taken by the signature as a discrimination threshold. Optimal cut-off corresponds to the most effective signature discrimination threshold and it could be measured by several methods. One method to find the optimal cut-off could be by using the Youden index. It corresponds to the value that maximizes the Youden index as defined as the sum of the sensitivity and specificity for each possible value of the signature. 95% confidence intervals were determined according to the Delong method in this example, but can be also assessed by a bootstrapping method.

The method of the invention, and the radiomics-based signature of the invention are able to discriminate between responders and non-responder patients suffering in particular from carcinomas, toward immunotherapeutic treatments such as anti-PD1 and anti-PD-L1 immune checkpoint blockers.

In this method, only the acquisition of the target features with the imaging device requires a physical contact with the patient. All the next steps can be performed with computer devices, in silico, or by individuals.

This method is non-invasive, by contrast with all the other existing methods in the art requesting a prior biopsy of a sample of the solid tumor.

The method of the invention is advantageously used to predict the outcome of cancer patients. It requires the use of non-invasive imagining technologies such as scanners, magnetic resonance imaging (MRI) or PET (Positron Emission Tomography), so as to generate the "radiological image" of the ROI.

The method of the invention can contain other steps such as using genomic data, feature extraction of tumor and rim, and machine-learning. Preferably, it does not contain any invasive step. In particular, it does not require any biopsy nor blood collection step.

Said method uses computational medical imaging and can be also called "radiomics-based CD8+ score" (in the context of the invention, the term "radiomics" stands for "medical image processing and analysis"). It is a novel marker of the efficacy of immunotherapy in patients in need for said treatment.

The present inventors identified at least two different signatures of at least 6 radiomics features able to detect the tumor immune infiltrates and having prognostic value as exposed above. These two signatures are detailed in examples 1 and 2 below. The first signature (example 1) has been determined and validated on a cohort of patients suffering from a specific cancer, a head and neck carcinoma. It is therefore more useful for this particular category of patients. By contrast, the second signature (example 2) has been determined and validated on cohorts containing patients suffering from different types of cancers (Tables 9 to 14). It is therefore more generic and can be applied to any cancer patients suffering from a solid tumor.

The signatures can be reproduced as explained in the examples. Briefly, CTs were selected if the slice-thickness was ≤5 mm and images were reconstructed using soft or standard reconstruction algorithms. Volumes of interest (VOI) for the radiomic analysis consisted of the tumor volume and a peripheral ring, which was created around the tumor margins using 3D expansion and shrinkage of 2 mm on both sides (i.e. inner and outer), resulting in a 4 mm thickness 3D ring around the tumor. An image processing step has been done to normalize the images. Voxels were resampled to 1×1×1 mm3, and Hounsfield values of the images were regrouped into one discrete value for every 10UH (absolute discretization). Variables computationally extracted from the images consisted of radiomics features from tumor and ring, VOI location and variables related to the imaging acquisition. A machine learning algorithm was used to train a radiomic signature to predict the estimation of CD8 T-cells and validation datasets were used to validate this signature on a genomics, phenotype and clinical level.

In a first preferred embodiment, the signature of the invention contains 5 radiomics features from the tumor, and one radiomic feature from the ring of the tumor.

A peritumoral region ("ring") may be defined as the region surrounding the tumoral region at a specified distance from the tumor borders. For example, in one embodiment, the peritumoral region may be defined as the region extending 2 mm from the external and internal tumoral borders creating a form of 4 mm in diameter enclosing the tumor borders. In another embodiment, the peritumoral region may be the region extending 5 mm from the tumoral boundary, or 10 mm from the tumoral boundary. The peritumoral region may be defined by a distance measured in mm, or in other units, including pixels or voxels.

These 5 tumor specific features or "variables" can consist in energyH, correlation, maxValue, Contrast.1, and SZHGE and the peripheral feature can consist in maxValue, as defined in the LIFEX [43].

TABLE 2

| Features of signature 1 |
| --- |
| energyH |
| correlation |
| maxValue for the tumor |
| maxValue for the ring |
| Contrast. 1 |
| SZHGE |

Said radiomic score is calculated by means of a random forest type calculation, then compared with a reference value so as to determine, for each analyzed patient:

if the tumor immune infiltrate is high or low, if said patient will respond to an anti-cancer treatment (e.g., an immunotherapeutic treatment as defined above), and/or if his/her overall survival is likely to be long or short when treated with said anti-cancer treatment.

In a second preferred embodiment, the signature of the invention can contain 2 radiomics features from the tumor, 3 radiomic features from the ring of the tumor, 2 radiomics features from the localization variables (VOI) and one acquisition-dependent variable.

These tumor specific features or "variables" can be minValue, and GLRLM_SRHGE.

The ring specific features or "variables" can be GLRLM_SRLGE, GLRLM_LGRE and GLRLM_LRLGE.

The localisation variables can be VOI_Adenopathy and VOI_head_and_neck.

The acquisition variable can be kVp (kiloVoltage peak).

The radiomic-based signature of the invention may specifically contain:

at least one conventional variable such as minValue, at least one Gray-level Run Length Matrix (GLRLM) variable, at least one acquisition marker such as kVp, at least one localization marker such as VOI.

The radiomic-based signature of the invention may more specifically contain:

one conventional variable such as minValue, four Gray-level Run Length Matrix (GLRLM) variables, one acquisition marker such as kVp, two localization markers such as VOI.

The radiomic-based signature of the invention may even more specifically contain:

the minValue for the tumor as conventional variable, four Gray-level Run Length Matrix (GLRLM) variables consisting of: GLRLM_SRHGE, GLRLM_SRLGE, GLRLM_LGRE and GLRLM_LRLGE, the acquisition marker kVp, and two localization markers consisting of: VOI_Adenopathy and VOI_head_and_neck.

When computed in particular with the coefficients presented in Table 3, it is possible to calculate a radiomic score=$a_1X_1+a_2X_2+ \ldots +a_iX_i+b$ With:

$a_i$=coefficient of the variable i $X_i$=value of the variable i determined from the input image b=intercept (typically 3,413472 in the example 2 below)

TABLE 3

| Features | Coefficient |
| --- | --- |
| minValue | −0.5133 |
| GLRLM_SRHGE | −0.1380 |
| GLRLM_LGRE | 0.0839 |
| GLRLM_SRLGE | 0.1049 |
| GLRLM_LRLGE | 0.1216 |
| VOI_Adenopathy | 0.4286 |
| VOI_head_and_neck | −0.3673 |
| kVp | −0.0109 |

Figure 8:

It is notable that the signature included kVp and VOI locations. Retaining kVp highlights the need to account for image acquisition variability when cohorts are heterogenous, given that textural features are highly dependent on it [51, 57]. VOI locations were included by design to account for radiomic information likely related only to the organ analyzed since it is recognized that tissue origin exerts a major impact on the tumor immune contexture [58]. The machine learning model retained three groups: adenopathy, head and neck, and the rest. A sensitivity analysis was performed without the non-radiomic variables and showed poorer results, underscoring the importance of adjusting to these parameters when developing radiomics predictive tools (FIG. 8).

Said radiomic score is then compared with a reference value so as to determine, for each analyzed patient:

if the tumor immune infiltrate is high or low, if said patient will respond to an anti-cancer treatment (e.g., an immunotherapeutic treatment as defined above), and/or if his/her overall survival is likely to be long or short when treated with said anti-cancer treatment.

The method of the invention extract radiomic features (e.g. quantitative image descriptors) from radiological images to generate predictive and prognostic information, and thus provide non-invasive biomarkers for treatment response, monitoring patients, disease prognosis, and personalized treatment planning. The extracted radiomic features are then preferably provided to a machine learning predictor which predicts a quantitative score of the CD8 T-cells infiltration in the region of interest. The classification can then be achieved by the user in view of this score and according to a cut-off which is to be determined depending on the cohort of patient analyzed.

The methods of the invention enable to generate a personalized treatment plan. The personalized treatment plan is based on the high or low score of CD8+ T cells. The personalized treatment plan may include an immunotherapy recommendation, an immunotherapy schedule, an immunotherapy dosage value, a follow up treatment schedule, or other action. The personalized treatment plan may include information that facilitates developing a precision treatment plan for a patient associated with the radiological image. For example, upon determining that a tumor is classified as a responder, the method of the invention may control the personalized cancer treatment system to generate a first personalized treatment plan that indicates a first type of therapy. Upon determining that the tumor is classified as a non-responder to this first therapy, the method may generate a second, different personalized treatment plan that proposes a second, different type of therapy.

By increasing the accuracy with which response to immunotherapy is predicted, the methods of the invention produce the concrete, real-world technical effect of reducing the amount of unnecessary biopsies or other invasive procedures for patients who are unlikely to benefit from immunotherapy treatment. Additionally, these methods reduce the expenditure of time, money and therapeutic resources on patients who are unlikely to benefit from the treatment. They thus improve on conventional approaches to predicting response to immunotherapy in a measurable, clinically significant way.

In another aspect, the present invention relates to a computer-readable storage device that may store computer executable instructions that if executed by a machine (e.g., computer, processor) cause the machine to perform the methods of the invention.

Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a solid state device (SSD), a memory stick, a data storage device, and other media from which a computer, a processor, on the cloud in a SAS mode or other electronic device can read.

By displaying the annotated image of the ROI, the classification, or the features, the apparatus of the invention provides a timely and intuitive way for a human pathologist, a personalized cancer treatment system, or a diagnostic system to more accurately predict response to immunotherapy, thus improving on conventional approaches to predicting response to treatment.

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

FIGURE LEGENDS

FIG. 1. Radiomics-based CD8+ score according to postulated groups of tumors.

Figure 2:
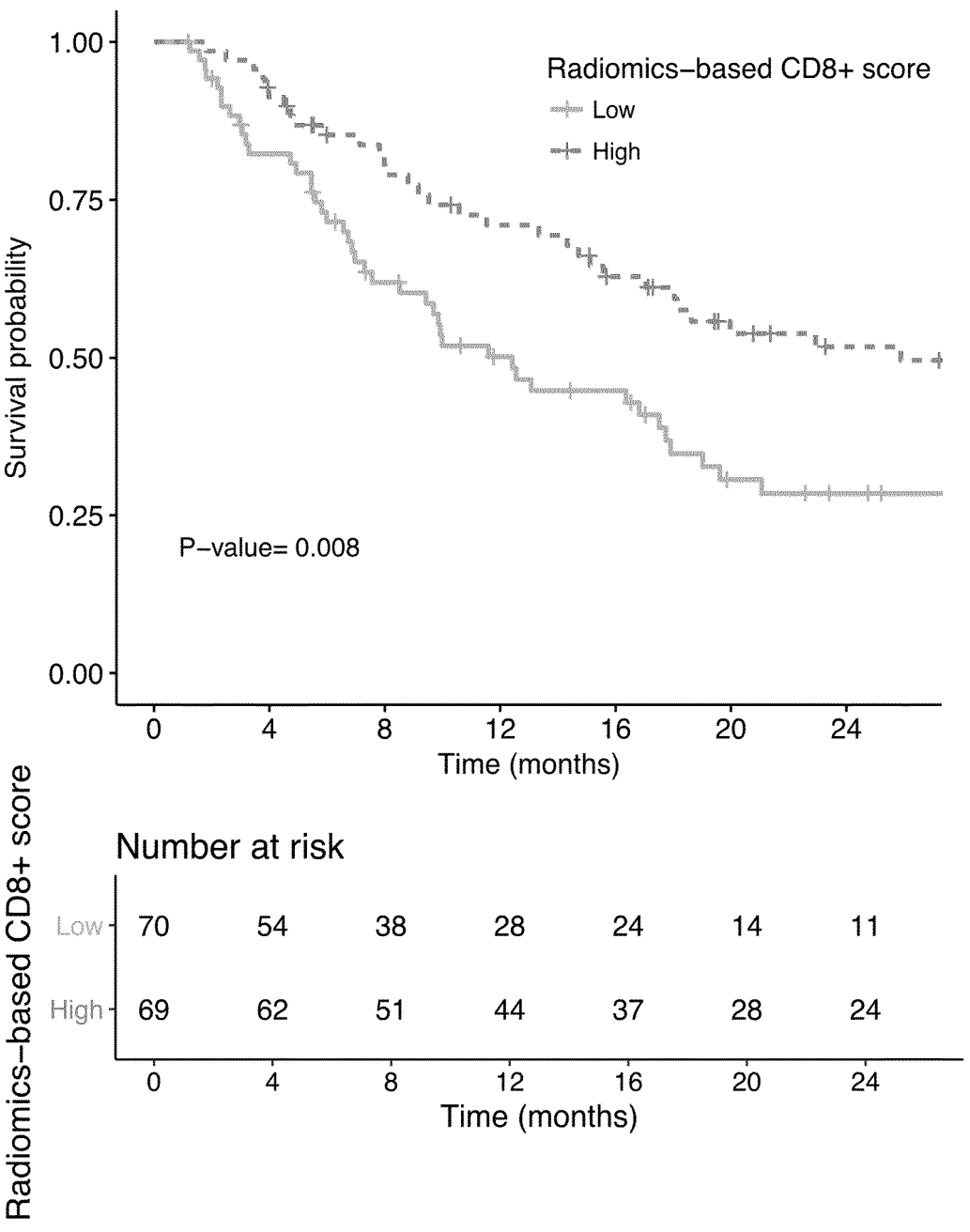

FIG. 2. Overall survival curves of the patients treated with anti-PD-1/PD-L1 according to the radiomics-based CD8 score of example 1.

Figure 3:
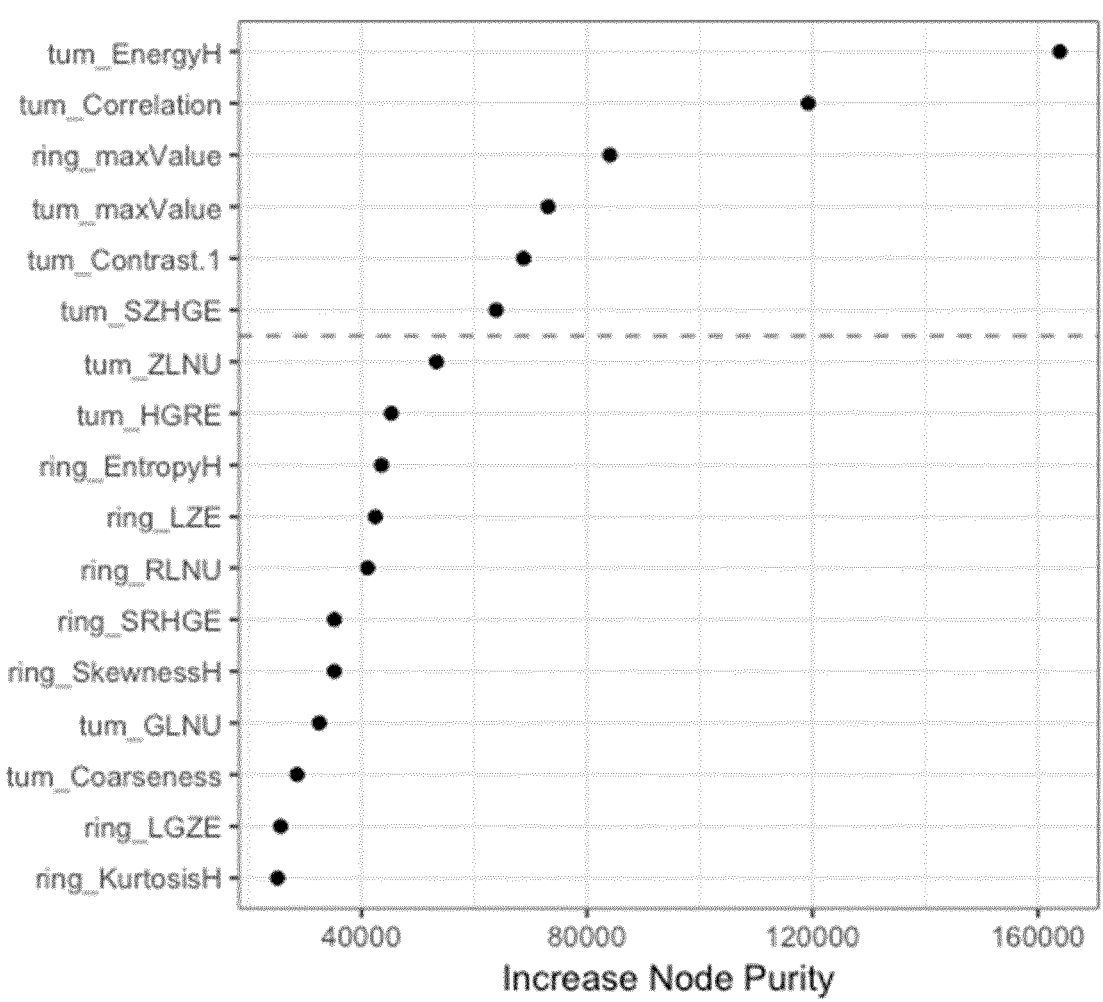

FIG. 3. Importance of the different features in the random forest model of example 1.

Figure 4:
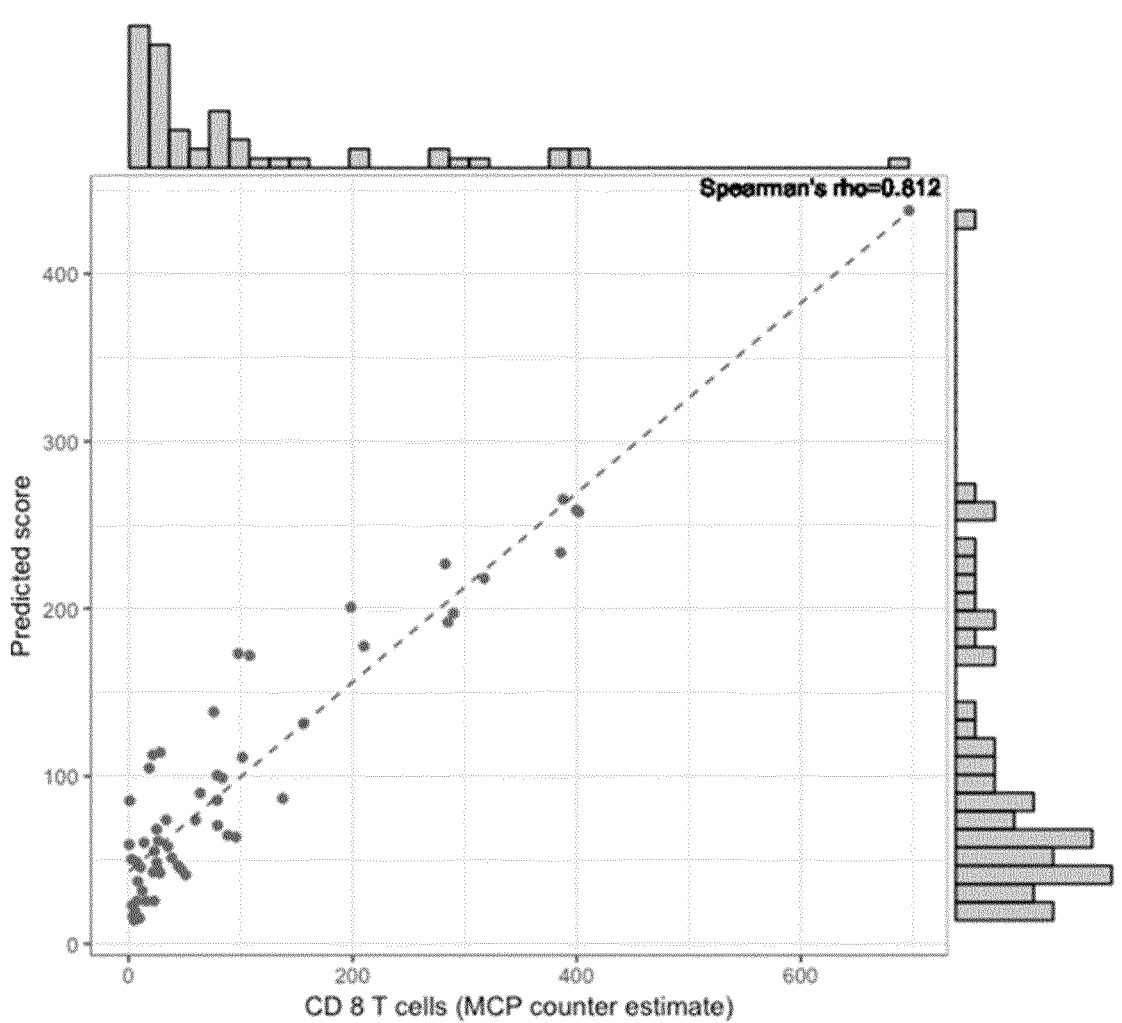

FIG. 4. Internal validation of the signature of example 1.

Figure 5:
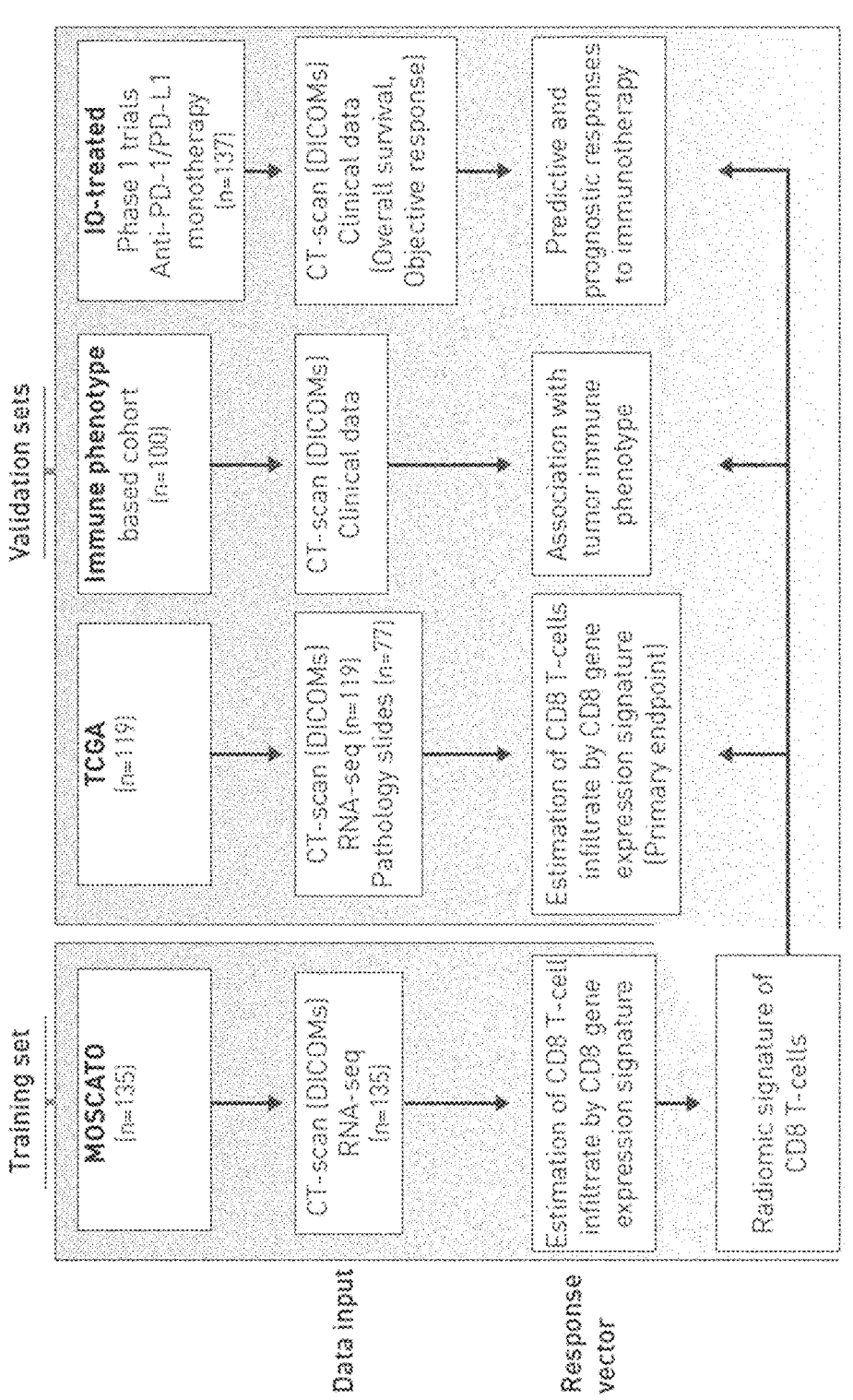

FIG. 5. Study design of the assay of example 2.

Figure 6A:
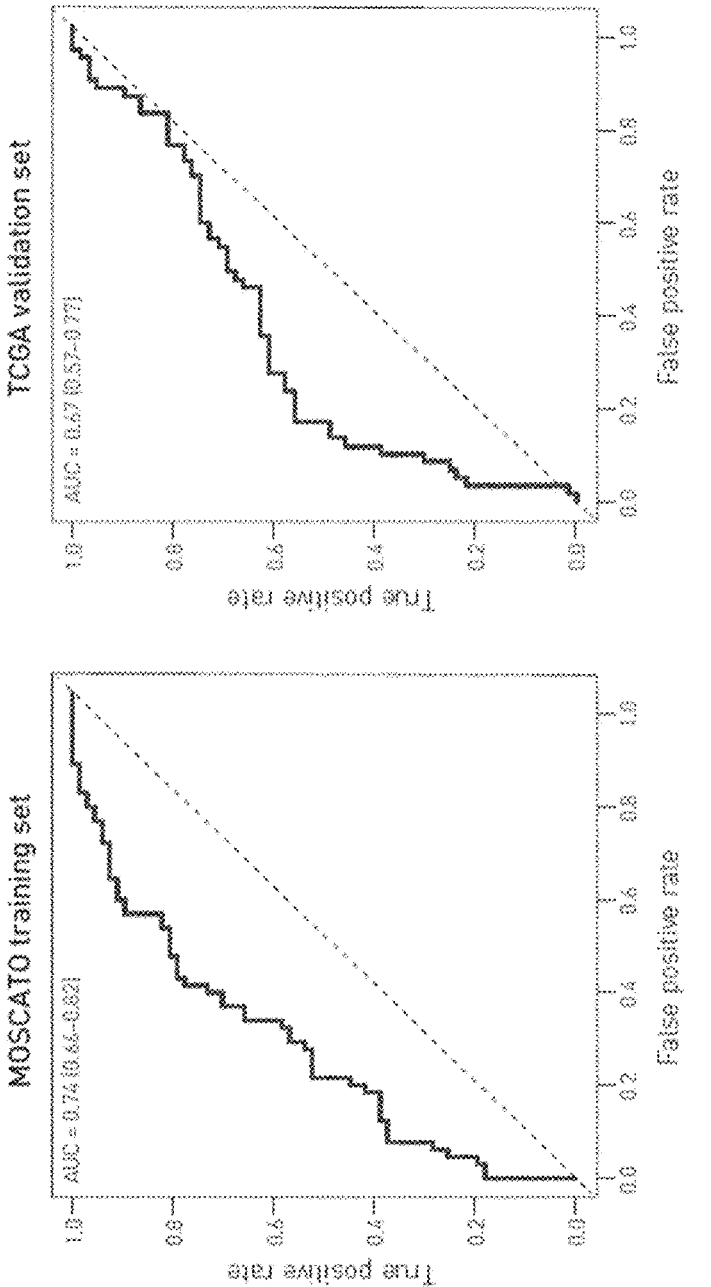
Figure 6A:
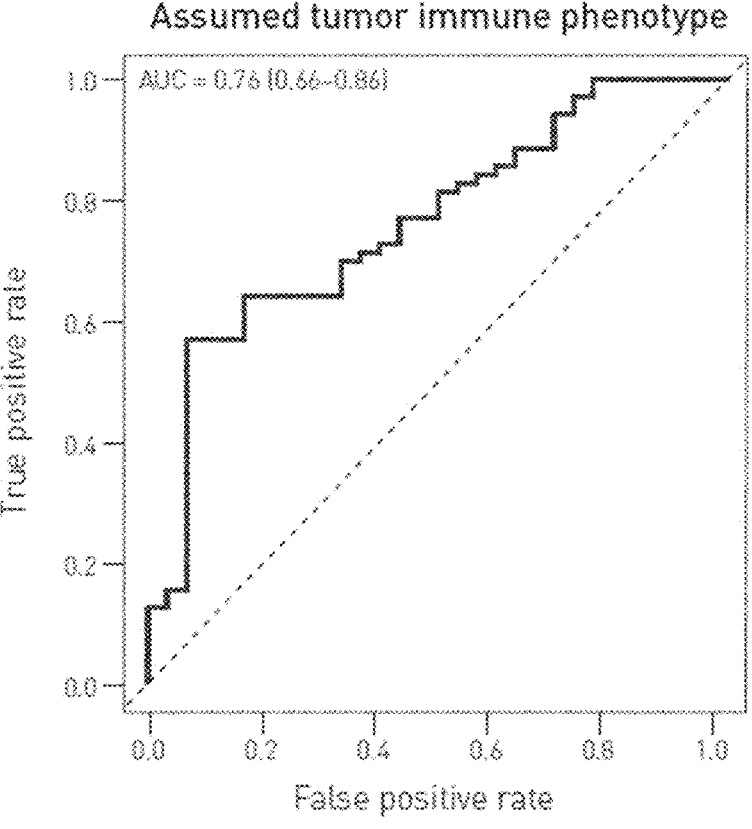
Figure 6B:
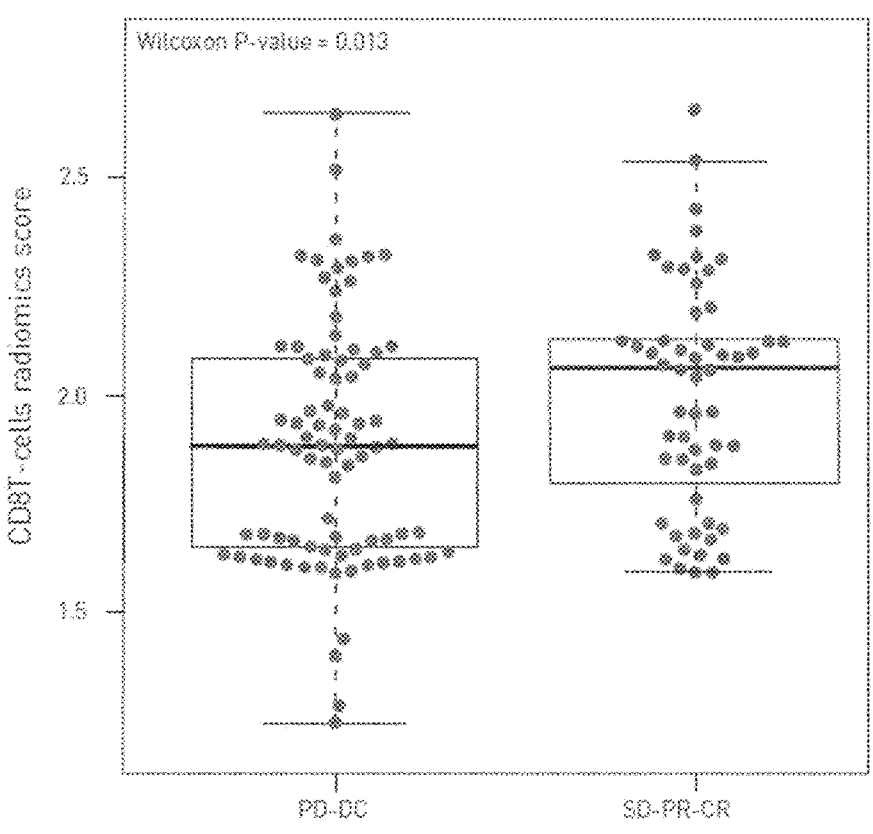
Figure 6B:
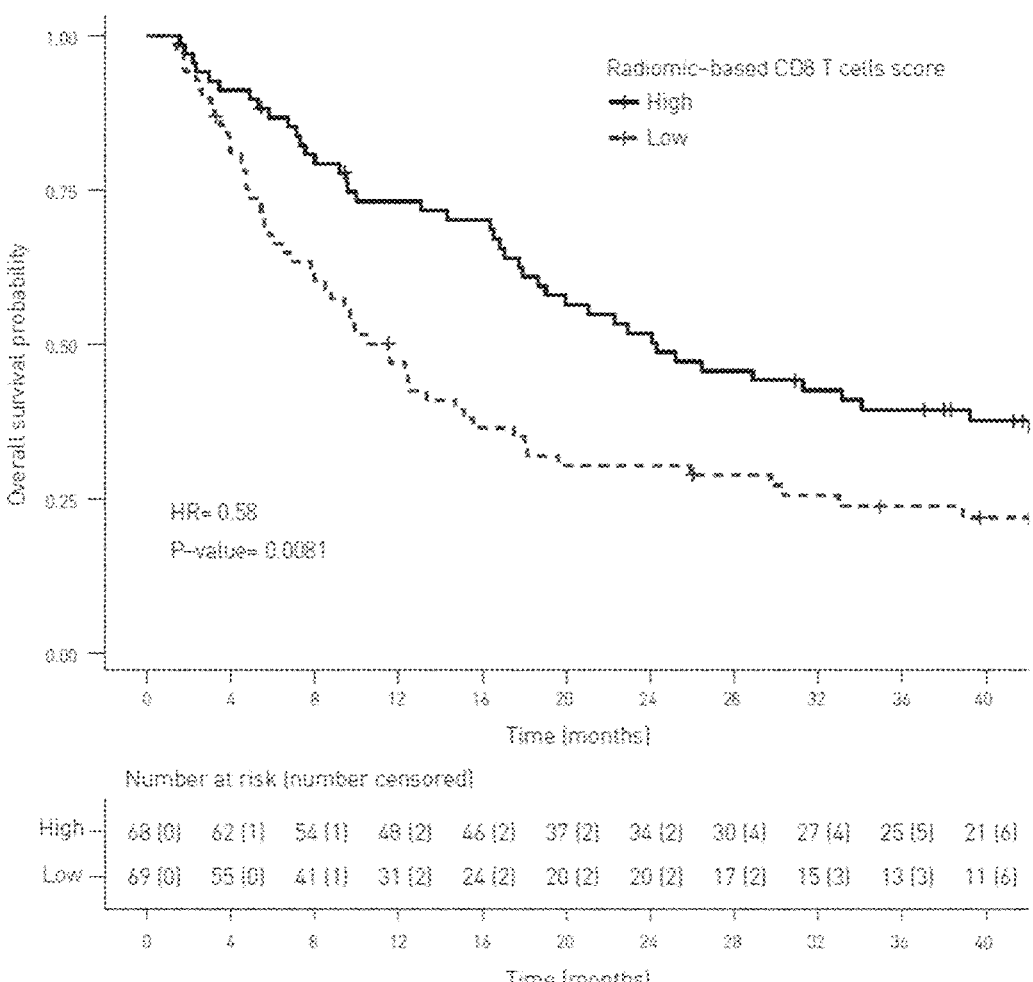

FIGS. 6A-6B. Performance of the radiomic signature of example 2 in training and validation datasets.

FIG 6A: Area under the curve (AUC) of the receiver operator characteristic of radiomic-scores in MOSCATO training set, TCGA validation set, immune phenotype-based dataset.

FIG 6B: Objective response to anti-PD-1/anti-PD-L1 monotherapy at 6 months according to the CD8 T-cells radiomic score, and overall survival of patients according to the radiomic score (high/low defined by the median value). PD: stable disease; DC: disease control; SD: stable disease; PR: partial response; CR: complete response.

Figure 7:
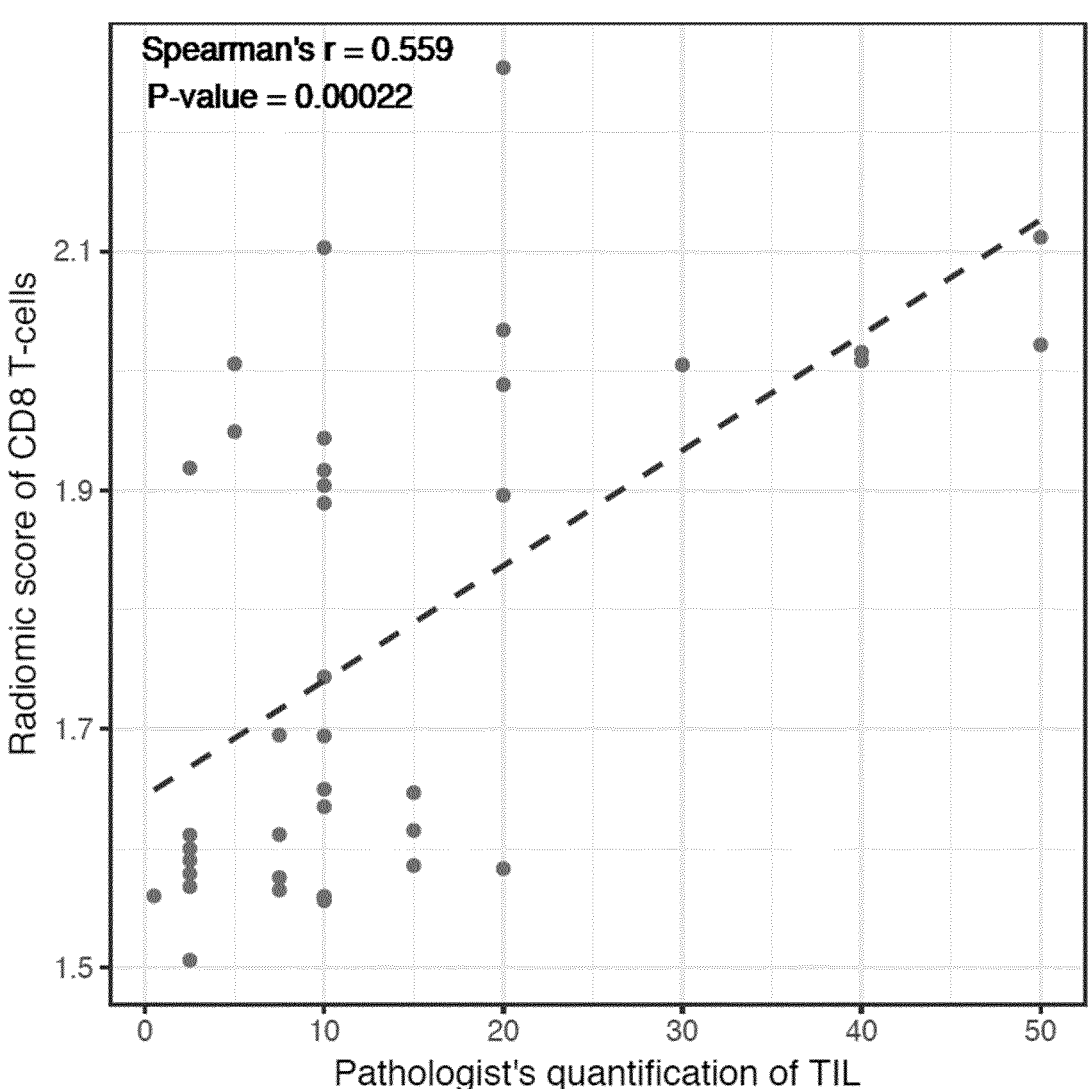
Figure 7:
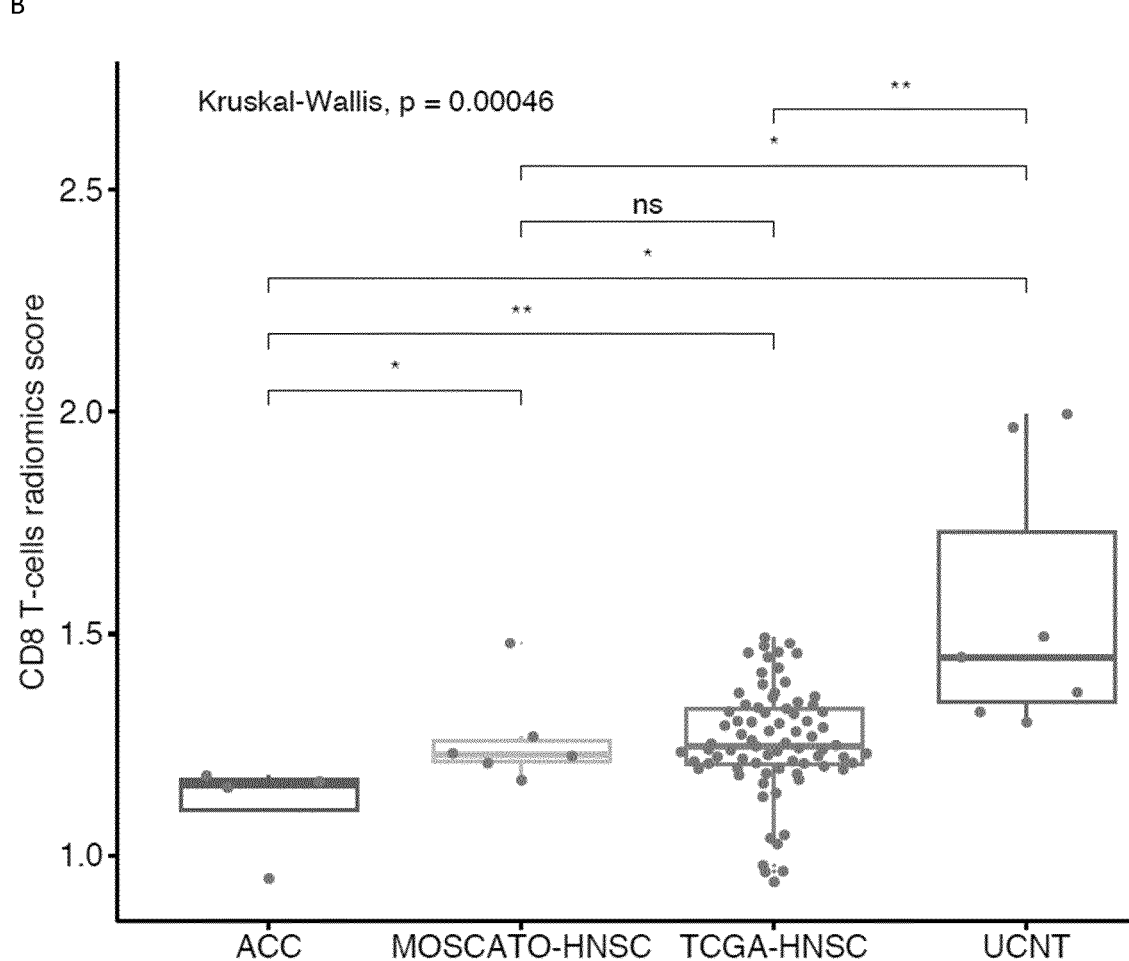

FIG. 7. Evaluation of agreement between radiomic score of CD8 T-cells of example 2 and pathology A. CD8 T-cells radiomic score as a function of the pathologist's semi-quantitative quantification of tumor infiltrating lymphocytes (TILs) in the TCGA-cohort, including patients with bladder cancer (BLCA), liver hepatocellular carcinoma (LIHC), lung adenocarcinoma (LUAD) and lung squamous cell carcinoma (LUSC).

B. CD8 T-cells radiomic score according to the tumor type in head and neck tumors. HNSCC were retrieved from MOSCATO cohort (n=6) and TCGA cohort (n=76), and adenoid cystic carcinoma (ACC) from the immunephenotype cohort (n=4). Seven patients with undifferentiated carcinoma of nasopharyngeal type (UCNT) from our institute (known to be very immune inflamed) were added for this post-hoc analysis.

FIG. 8. Performance of the radiomic signatures in function of the inclusion of non-radiomics variables in the model (kVp and VOI localization). These figures show that without the non-radiomics variables, performances of the radiomic signature are lower, even with a lower penalization of the model.

Figure 9:
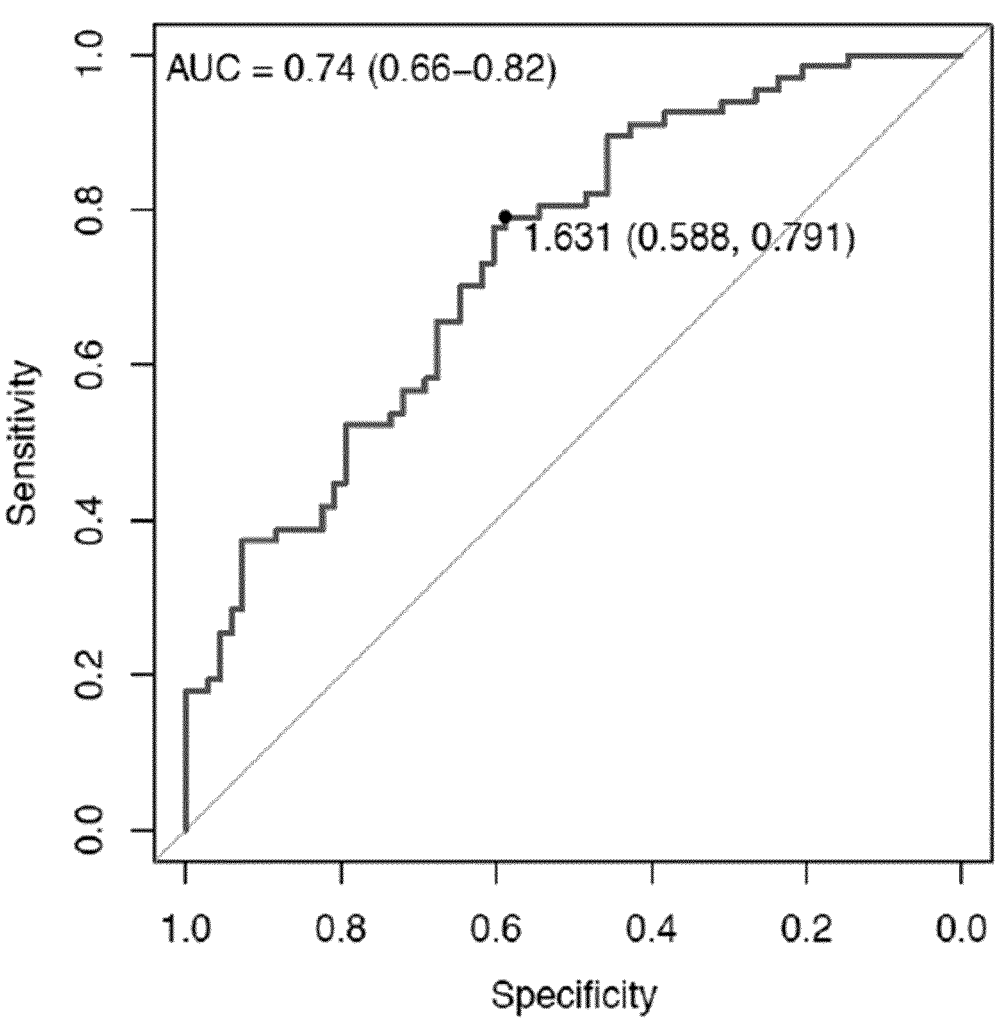

FIG. 9. Performance of the radiomic signature in the MOSCATO training dataset. A cutoff was determined according to the Youden index (1.631).

EXAMPLES

Example 1: Contrast-Enhanced Computer Tomography (CT) Imaging of Head and Neck Carcinomas Training Set Clinical and imaging data of the head and neck squamous cell carcinoma cohort provided by The Cancer Imaging Archive (http://www.cancerimagingarchive.net/) (TCIA-HNSC) were used [35, 36]. Baseline contrast-enhanced computer tomography (CT) imaging with slice-thickness equal to or less than 5 mm and acquired using 120 KVP were reviewed. After exclusion of patients who had only postoperative images or artifacts at the tumor level, no gantry-tilt (for technical compatibility of our texture imaging software), and no genomic data available, 57 patients were included.

Corresponding genomic data were obtained from The Cancer Genome Atlas (TCGA) portal (https://portal.udc-.cancer.gov/) and consisted of 20530 genes obtained with Illumina HiSeq RNASeqV2 (Illumina, San Diego, CA, USA) and quantified using RPKM (Reads Per Kilobase Million) method. The population abundance of tissue-infiltrating CD8 T cells was estimated using the MCPcounter R package [37].

Tumor Segmentation and Feature Extraction

Each primary tumor was manually delineated on CT-scan images by two radiation oncologists using ISOgray® segmentation solution (Dosisoft, Cachan, France). A peripheral ring was created around the tumor margins using 3D expansion and shrinkage of 2 mm on both sides (inner and outer) to take into account the peri-tumoral stroma and the invasion margins. Large vessels and neighboring organs were excluded from the ring if they were not involved by the tumor (not shown).

Radiomics feature extraction was performed using the LIFEx software (Local Image Feature Extraction, www.lifexsoft.org) [38]. Thirty-eight first and second order features were extracted for each of the two volumes of interest (VOI, tumor and ring) leading to a total of 76 features. Hounsfield-units (HU) values in the VOIs were then resampled into 400 discrete values using absolute discretization. The minimum and maximum bounds of the resampling intervals were set to −1000 and 3000 HU, leading to a bin size of 10 HU. Four gray-level matrices were calculated in each VOI: the Gray-Level Co-occurrence Matrix (GLCM), the Gray-Level Run Length Matrix (GLRLM), the Neighborhood Gray-Level Different Matrix (NGLDM) and the Gray-Level Zone Length Matrix (GLZLM). GLCM and GLRLM were first computed in 13 directions to account for all independent directions between one voxel and its 26 neighbors [39]. Each textural feature extracted from these matrices corresponds to the average value over the 13 directions.

Feature Selection and Machine Learning Model

Feature selection was done by first eliminating correlated and redundant variables (Pearson's rho>0.75) using the Caret R package (version 6.0-76) [40]. Then, a random forest model was used on the remaining radiomic feature variables to predict the CD8 T cells abundance estimated by MCP-counter, using the RandomForest R package (version 4.6-12), and 500 trees [41]. The optimal number of variables randomly sampled as candidates at each split (mtry) was defined using the "tuneRF" function in this package. Variables were ranked according to their importance estimated by the IncNodePurity approach, which corresponds to the total decrease in node impurities, measured by the Gini index from splitting on the variable, averaged over all trees. The six radiomic features with the largest IncNodePurity were selected to train the final random forest model to predict a CD8 T cells quantitative score.

Validation Cohort

This signature was validated on two independent cohorts. The first consists of 100 randomly selected patients from our institute database, for which the pathologic abundance of tumor immune infiltrate was postulated as either favorable based on documented good response to immunotherapy in the literature or if the VOI was a lymph node (lymphoma, melanoma, lung, bladder, renal and MSI+ cancers; 70 patients), or unfavorable if otherwise (adenoid cystic carcinoma, low-grade neuroendocrine tumors, uterine leiomyosarcoma; 30 patients). In this "postulated-cohort", the bigger lesion, either primary or metastatic, was delineated as previously described (tumor and ring) on contrast-enhanced CT-scan images with a slice thickness of less than or equal to 5 mm.

Exploratory Analyses

A third independent cohort of consecutive patients prospectively enrolled in immuno-oncology phase 1 trials (anti PD-1/PD-L1 monotherapy) at Gustave Roussy between December 2011 and January 2014 (IO) was analyzed to infer the relationship of this radiomics signature with patient outcome (Overall Survival). This cohort was previously described and published elsewhere [44]. A total of 139 patients who had a baseline contrast-enhanced CT-scan images with a slice thickness ≤5 mm were included. One target lesion defined by the radiologist according to RECIST 1.1 was delineated for each patient. Follow-up and survival times were calculated from the baseline date. The median of the radiomics-based CD8+ score was used to separate patients from this cohort into two groups.

Finally, the signature was applied on two clinical cases from the cohort of patients treated with immunotherapy to assess its relationship with spatial heterogeneity through correlations with sequential pathological analyses, and with temporal heterogeneity by repeated measure or the radiomics-based score through the course of the disease.

Statistical Analysis

Comparisons between variables were performed using Wilcoxon signed-rank tests or Kruskall-Wallis test for numerical variables, and fisher tests for categorical variables. Correlations were assessed by Spearman's correlation coefficient. Overall survival was computed according to the Kaplan-Meier method and Cox's proportional-hazards survival estimates. A threshold of <0.05 was defined for double tailed P-value's significance. Statistical analyses were carried out using R software version 3.4.0 (https://www.r-project.org/) [45].

Development of a Radiomics Signature Predicting Tumor Immune Infiltration Based on CT-Scans Characteristics of the patients from the training cohort (TCIA-HNSC cohort (n=57)) are summarized in TABLE 4. Evaluation of CD8 T cells abundance of patients was done using MCP-counter (mean±sd=101.5±140.0).

TABLE 4

| | Category | Overall |
|---|---|---|
| n | | 57 |
| Age (median [IQR]) | | 59.00 [50.00, 67.00] |
| Gender (%) | Female | 13 (22.8) |
| | Male | 44 (77.2) |
| Tumor localization (%) | Alveolar Ridge | 2 (3.5) |
| | Base of tongue | 5 (8.8) |
| | Buccal Mucosa | 1 (1.8) |
| | Floor of mouth | 5 (8.8) |
| | Hard Palate | 1 (1.8) |
| | Hypopharynx | 1 (1.8) |
| | Larynx | 14 (24.6) |
| | Oral Cavity | 7 (12.3) |
| | Oral Tongue | 10 (17.5) |
| | Tonsil | 11 (19.3) |

TABLE 4-continued

| | Category | Overall |
|---|---|---|
| Clinical T (%) | T1 | 2 (3.5) |
| | T2 | 14 (24.6) |
| | T3 | 22 (38.6) |
| | T4a | 18 (31.6) |
| | T4b | 1 (1.8) |
| CD8+ T cell abundance by MCP-counter (median [IQR]) | | 38.39 [15.68, 101.54] |

After removing redundant variables, 17 remained. The final CD8+ radiomics-based signature obtained after random forest consisted of five features from the tumor (energy, correlation, max value, NGLDM contrast, short-zone high grey-level emphasis [SZHGE]) and one from the ring (max value) (FIG. 3). The predicted radiomics-based CD8+ score in this cohort was: mean±sd=100.3±83.8. As internal validation, the correlation of this signature with the estimated TCGA CD8 was spearman's rho=0.81 (P<1 e-05) (FIG. 4).

External Validation

When applied to the postulated-cohort (TABLE 5), the radiomics-based CD8+ score was significantly higher in the favorable tumor immune infiltrate group (Wilcoxon's P-value=3.4 e-04) with an area under the curve (AUC) of 0.73, 95% CI [0.62, 0.83] (FIG. 1).

TABLE 5

| | Category | Unfavorable | Favorable |
|---|---|---|---|
| N = 100 | | 30 | 70 |
| Histology (%) | Adenoid cystic carcinoma | 4 (13.3) | 0 (0.0) |
| | Colorectal | 2 (6.7) | 25 (35.7) |
| | Gynecological | 0 (0.0) | 1 (1.4) |
| | Kidney | 0 (0.0) | 3 (4.3) |
| | Leiomyoma | 7 (23.3) | 0 (0.0) |
| | Lung | 0 (0.0) | 6 (8.6) |
| | Lymphoma | 0 (0.0) | 25 (35.7) |
| | Melanoma | 0 (0.0) | 8 (11.4) |
| | Neuroendocrine | 17 (56.7) | 0 (0.0) |
| | Anal epidermoid carcinoma | 0 (0.0) | 1 (1.4) |
| | Urothelial | 0 (0.0) | 1 (1.4) |
| VOI (%) | Abdominopelvic and subcutaneous | 8 (26.7) | 10 (14.3) |
| | Adenopathy | 0 (0.0) | 37 (52.9) |
| | Brain | 0 (0.0) | 8 (11.4) |
| | Head and neck | 4 (13.3) | 0 (0.0) |
| | Liver | 10 (33.3) | 10 (14.3) |
| | Lung | 8 (26.7) | 3 (4.3) |
| | Mediastinum | 0 (0.0) | 2 (2.9) |
| MSI (%) | No | 30 (100.0) | 58 (82.9) |
| | Yes | 0 (0.0) | 12 (17.1) |

(VOI = Volume of interest, MSI = Microsatellite instability)

Exploratory Analyses

Survival Prediction of Patients Treated by Immunotherapy

To infer whether the radiomics-based CD8+ score could predict the response to immunotherapy, this score was applied in the cohort of patients treated with immunotherapy. Patient characteristics are summarized in TABLE 7.

TABLE 7

| | level | Radiomics-based CD8+ score | | p | Test |
| | | Low | High | | |
|---|---|---|---|---|---|
| N = 139 | | 70 | 69 | | |
| Age (median [IQR]) | | 55.5 [45.0, 65.0] | 61.0 [49.0, 67.0] | 0.367 | Wilcoxon |
| Gender (%) | Female | 35 (50.0) | 28 (40.6) | 0.308 | Fisher |
| | Male | 35 (50.0) | 41 (59.4) | | |
| Royal Marden | 0 | 13 (18.6) | 19 (27.5) | 0.670 | Fisher |
| Score (%) | 1 | 26 (37.1) | 22 (31.9) | | |
| | 2 | 26 (37.1) | 23 (33.3) | | |
| | 3 | 5 (7.1) | 5 (7.2) | | |
| Number of lines before inclusion (median [IQR]) | | 2.0 [1.0, 3.8] | 2.00 [1.0, 4.0] | 0.842 | Wilcoxon |
| Histology (%) | Melanoma | 18 (25.7) | 28 (40.6) | 0.812 | Fisher |
| | Lung | 10 (14.3) | 8 (11.6) | | |
| | Urothellial | 7 (10.0) | 5 (7.2) | | |
| | Kidney | 7 (10.0) | 4 (5.8) | | |
| | Gynaecological | 5 (7.1) | 4 (5.8) | | |
| | Liver | 6 (8.6) | 2 (2.9) | | |
| | Lymphoma | 3 (4.3) | 4 (5.8) | | |
| | Breast | 3 (4.3) | 3 (4.3) | | |
| | Colorectal | 3 (4.3) | 3 (4.3) | | |
| | Head_neck | 3 (4.3) | 2 (2.9) | | |
| | Other | 5 (7.1) | 6 (8.7) | | |
| VOI | Adenopathy | 19 (27.1) | 19 (27.5) | 0.213 | Fisher |
| | Liver | 21 (30.0) | 17 (24.6) | | |
| localization (%) | Lung | 8 (11.4) | 16 (23.2) | | |
| | Abdominopelvic or subcutaneous | 9 (12.9) | 12 (17.4) | | |
| | Mediastinum | 10 (14.3) | 4 (5.8) | | |
| | Breast | 1 (1.4) | 1 (1.4) | | |
| | Head and neck | 2 (2.9) | 0 (0.0) | | |
| Radiomics-based CD8+ score (median [IQR]) | | 63.20 [51.96, 81.87] | 155.36 [123.08, 188.61] | <0.001 | Wilcoxon |

(IQR = interquartile range)

Median follow-up time was 13.1 months, interquartile range (IQR) [5.7, 24.1]. Median OS was 17.7 months, 95% CI [13.3, 25.9]. The median of the radiomics-based CD8+ score in this cohort was 109.6. OS was significantly higher in patients with a high CD8+ score (median OS=25.9 vs 12.4 months, HR=0.55, 95% CI [0.36, 0.86], P-value=8.7 e-03) (FIG. 2). This prognosis value stayed significant when including the RMH score at baseline in a multivariate analysis (TABLE 8).

TABLE 8

| | Overall Survival Multivariate analysis | | |
| | Hazard Ratio | 95% CI | P-value |
|---|---|---|---|
| RMH 2-3 | 2.05 | 1.31-3.19 | 1.6e-03 |
| radiomics-based CD8+ score | 0.50 | 0.32-0.78 | 2.6e-03 |

(RMH: Royal Marsden Hospital prognostic score. Significant p-value in bold.)

A subgroup analysis according to histology did not identify a group for which the score performance was better. In terms of tumor location, the performance of the score seemed better for the subgroup of abdominopelvic and subcutaneous VOIs (HR=0.28, 95% CI [0.09, 0.94], P-value=0.04) (not shown).

Spatial and Temporal Heterogeneity

To assess whether this radiomics-based CD8+ score could be useful for spatial heterogeneity assessment and patient monitoring, this signature was applied for two patients with uncommon responses to immunotherapy from the cohort of patients treated with immunotherapy.

Patient 1 is a 42 year-old woman with colon cancer and liver metastases treated with immunotherapy. She underwent stereotactic radiation therapy of one liver metastasis (segment 6) with the aim of inducing abscopal response. Three months later, the liver metastases progressed, but the morphology of the irradiated lesion significantly changed, showing core necrosis and a rim of hypodensity. These changes were likewise seen in the non-irradiated lesion (segment 4) (not shown). Peripheral and central biopsies were done for both lesions. Using the cut-off used in the 10 cohort (median value), radiomics analysis concluded that the core and the peripheral regions of the irradiated lesion had low scores of CD8+ whereas the non-irradiated lesion had a high score for the peripheral region, and a low score for the core region (not shown). These assumptions were confirmed by the pathological analysis with immunohistochemical stains for CD8+ T cells (not shown).

Patients 2 had metastatic head and neck cancers and was treated with anti-PD-1. He exhibited dissociated responses, with progression of cervical lesions, but marked objective responses of non-cervical secondary lesions (pulmonary lesions). Radiomics analysis of cervical nodes and pulmonary lesions at baseline and during the follow-up showed persistently high CD8+ scores for pulmonary lesions and low score for cervical node (not shown).

Example 2: Contrast Enhanced CT-Based Radiomics Signature of Different Solid Tumors Radiomic features were extracted from contrast-enhanced CTs of 135 patients with advanced solid malignant tumors from the prospective trial MOSCATO. For each patient, RNA-seq data were used to quantify CD8 T-cells. From 84 variables (78 radiomic features, 5 location variable, 1 technical variable), a radiomic-based predictor of CD8 T-cell expression was built using elastic-net. The primary objective was to confirm the relationship of this predictor with gene expression in an independent cohort of 119 patients from The Cancer Genome Atlas (TCGA). Two other independent cohorts of patients with solid tumors were used to evaluate this predictor: 100 patients with tumors assumed as either immune-inflamed (dense CD8 T-cell infiltration) or immune-desert (limited CD8 T-cell infiltration) to analyze the relevance with the immune-phenotype, and 137 patients treated with anti-PD-1/PD-L1 monotherapy in phase 1 trials to assess the relevance with clinical outcome.

A radiomic-signature of eight variables was determined. It was validated with the gene expression signature of CD8 T-cells in the TCGA dataset (AUC=0.67, P-value=0.0019), and the inflamed tumors in the assumed immune-phenotype cohort (AUC=0.76, P-value<0.0001). For patients treated with anti-PD-1/PD-L1, a high baseline radiomic-score was associated with higher objective response rate at 3 months, (P-value-0.049) and higher objective response rate and stable disease at 6 months (P-value=0.025 and 0.013, respectively). It was also associated with prolonged overall survival in univariate (median: 24.3 vs 11.5 mo., HR=0.58, 95% CI[0.39-0.87], P-value=0.0081), and multivariate analysis (P-value=0.0022).

This radiomic-signature of CD8 T-cells was shown to be relevant in three independent cohorts. It provided promising means to assess tumor immune phenotype and to infer outcomes for cancer patients treated with anti-PD-1/PD-L1.

Datasets

Radiomic analysis was applied retrospectively to four independent cohorts of patients above 18 years old with solid tumors (FIG. 5). Three cohorts refer to patients treated at Gustave Roussy while the last came from The Cancer Genome Atlas (TCGA) (https://cancergenome.nih.gov/) and The Cancer Imaging Archive (TCIA) databases (http://www.cancerimagingarchive.net/).

The MOSCATO dataset contains data from patients included in a precision medicine trial [42] and was used to train the radiomic signature. Three cohorts were used for validation. The TCGA dataset was constituted of RNA-seq data from The Cancer Genome Atlas, and the corresponding imaging data and pathology slides from The Cancer Imaging Archive and The Cancer Digital Slide Archive. The immune-phenotype based cohort contained tumors labeled as either immune-desert or inflamed. The IO (Immuno-Oncology) treated dataset was constituted of patients included in anti-PD-1/PD-L1 monotherapy phase 1 trials.

Training Set

The training dataset used to build the radiomic-signature of CD8 T-cells consisted of patients of the prospective MOSCATO trial (NCT01566019) where genomic information was obtained through computed tomography (CD-guided biopsy ([42]). In the "MOSCATO dataset", CT and RNA-seq data were available, allowing estimation of CD8 T-cells using RNA-seq data and radiomic analysis of the corresponding biopsied tumor images.

Validation Sets

Three different cohorts were used to assess the quality of the radiomic-signature. The TCGA dataset included patients for whom baseline preoperative imaging data with required quality standards and corresponding transcriptomic data were available ([36]). Five collections were used (Table 9): head and neck squamous cell carcinoma (TCGA-HNSC), lung squamous cell carcinoma (TCGA-LUSC), lung adeno-carcinoma (TCGA-LUAD), liver hepatocellular carcinoma (TCGA-LIHC), and bladder endothelial carcinoma (TCGA-BLCA). This dataset was used to validate the radiomic-signature.

TABLE 9

| | Category | Overall |
|---|---|---|
| N patients | | 119 |
| Age (median [IQR]) | | 61.00 [53.00, 70.00] |
| Gender (%) | Female | 34 (28.6) |
| | Male | 85 (71.4) |
| Cancer type (%) | Bladder | 11 (9.2) |
| | Head and neck | 76 (63.9) |
| | Hepatocellular carcinoma | 10 (8.4) |
| | Lung adenocarcinoma | 8 (6.7) |
| | Lung squamous cell carcinoma | 14 (11.8) |
| Genomic-based CD8 T-cells score (median [IQR]) | | 1.00 [0.52, 1.56] |

The "immune-phenotype dataset" consisted of randomly selected patients from our institute's database, representing the two extreme tumor immune phenotypes: inflamed or immune-desert, irrespective of treatment delivered. Inflamed tumors either had recognized sensitivity to immunotherapy, or had lymph nodes as volumes-of-interest (VOI) (lymphoma, melanoma, lung, bladder, renal and microsatellite instability-high (MSI+) cancers). Immune-desert tumors were those typically known to have poor lymphocyte infiltration (adenoid cystic carcinoma, low-grade neuroendocrine tumors, uterine leiomyosarcoma) (Table 10). Labeling of tumors was made by CF and EJL. This dataset was used to evaluate concordance of the radiomic-signature with tumor immune phenotype.

TABLE 10

| | Category | Immune-desert | Inflamed |
|---|---|---|---|
| N patients | | 30 | 70 |
| Age (median [IQR]) | | 54.00 [46.00, 67.75] | 56.00 [38.50, 67.75] |
| Gender (%) | Female | 20 (66.7) | 38 (54.3) |
| | Male | 10 (33.3) | 32 (45.7) |
| Histology (%) | Adenoid cystic carcinoma | 4 (13.3) | 0 (0.0) |
| | Colorectal | 2 (6.7) | 25 (35.7) |
| | Gynecological | 0 (0.0) | 1 (1.4) |
| | Kidney | 0 (0.0) | 3 (4.3) |
| | Leiomyoma | 7 (23.3) | 0 (0.0) |
| | Lung | 0 (0.0) | 6 (8.6) |
| | Lymphoma | 0 (0.0) | 25 (35.7) |
| | Melanoma | 0 (0.0) | 8 (11.4) |
| | Neuroendocrine | 17 (56.7) | 0 (0.0) |
| | Anal epidermoid carcinoma | 0 (0.0) | 1 (1.4) |
| | Urothelial | 0 (0.0) | 1 (1.4) |
| VOI location (%) | Adenopathy | 0 (0.0) | 39 (55.7) |
| | Liver | 10 (33.3) | 10 (14.3) |
| | Head and neck | 4 (13.3) | 0 (0.0) |
| | Abdominopelvic or subcutaneous | 8 (26.7) | 18 (25.7) |
| | Lung | 8 (26.7) | 3 (4.3) |
| MSI (%) | No | 30 (100.0) | 58 (82.9) |
| | Yes | 0 (0.0) | 12 (17.1) |
| Radiomic-score of CD8 T-cells (median [IQR]) | | 1.55 [1.50, 1.74] | 1.99 [1.59, 2.02] |

The IO-treated cohort consisted of consecutive patients enrolled in five immuno-oncology phase 1 trials (anti-PD-1/PD-L1 monotherapy) at Gustave Roussy (NCT01375842, NCT01358721, NCT01295827, NCT02054806, NCT01693562), details of which are available in previous publications ([44]). This cohort was used to infer the relationship of the radiomic-signature with patient response according to Response Evaluation Criteria In Solid Tumors (RECIST) version 1.1, progression-free survival (PFS) and overall survival (OS).

This study was approved by the institutional review board and conducted in accordance with ethical standards and the 1964 Helsinki declaration and its later amendments. Patients provided signed informed consent in accordance with their respective trial protocols.

Radiomic Features

For all cohorts, textural features were extracted from contrast-enhanced CTs. Images had slice-thickness ≤5 mm and soft or standard convolution kernel reconstruction (Table 11). Tumors were semi-automatically delineated by three radiation oncologists using ISOgray® (Dosisoft, Cachan, France). Segmented lesions corresponded to the biopsied lesion in MOSCATO, the primary lesion for TCGA, the biggest lesion (either primary or metastatic) for the immune-phenotype cohort, and one of the target lesions defined according to RECIST 1.1 by the radiologist (SA), blinded to the clinical data, for the IO-treated cohort.

"other" for subcutaneous or abdominal lesions. Tumor volume was included in analyses as a potential confounding factor.

Radiomic feature extraction was performed using LIFEx software version 3.44 (www.lifexsoft.org) ([38]). Images were resampled to 1×1×1 mm$^3$ voxels using 3D Lagrangian polygon interpolation. Hounsfield-units (HU) values through all the images were then resampled into 400 discrete values (called "bins") using absolute discretization from −1000 to 3000 HU, leading to a fixed bin size of 10 HU. Four gray-level matrices were calculated in 3D resulting to 39 radiomic features (first- and second-order features and volume) for each of the two VOIs (tumor and ring) (Table 1). Values of extracted radiomic features were normalized linearly in the range 0 to 1.

The Table 1 presents the radiomic features that have been extracted from the images. First-order features correspond to conventional indices and features extracted from the intensity histogram. Second-order or textural features have been also extracted from four textural matrices calculated using the LIFEx software (http://www.lifexsoft.org): the Gray-Level Co-occurrence Matrix (GLCM), the Gray-Level Run

TABLE 11

| | Category | MOSCATO | TCGA |
|---|---|---|---|
| Patients (n) | | 135 | 119 |
| Manufacturer (%) | GE MEDICAL SYSTEMS | 92 (68.1) | 51 (42.9) |
| | PHILIPS | 23 (17.0) | 30 (25.2) |
| | SIEMENS | 18 (13.3) | 33 (27.7) |
| | TOSHIBA | 2 (1.5) | 5 (4.2) |
| kVp (%) | 80 | 1 (0.7) | 0 (0.0) |
| | 100 | 31 (23.0) | 0 (0.0) |
| | 110 | 3 (2.2) | 0 (0.0) |
| | 120 | 94 (69.6) | 102 (85.7) |
| | 130 | 3 (2.2) | 4 (3.4) |
| | 140 | 3 (2.2) | 13 (10.9) |
| Slice | (median [IQR]) | 1.25 [1.25, 2.00] | 3.00 [2.00, 3.75] |
| Thickness | range | 0.625-5.0 | 1.0-5.0 |
| Pixel | (median [IQR]) | 0.73 [0.67, 0.82] | 0.55 [0.49, 0.70] |
| Spacing | range | 0.4355-0.9766 | 0.330-1.3672 |

| | Category | IO-treated | Tumor immune phenotype-based |
|---|---|---|---|
| Patients (n) | | 137 | 100 |
| Manufacturer (%) | GE MEDICAL SYSTEMS | 109 (79.6) | 39 (39.0) |
| | PHILIPS | 21 (15.3) | 8 (8.0) |
| | SIEMENS | 6 (4.4) | 53 (53.0) |
| | TOSHIBA | 1 (0.7) | 0 (0.0) |
| kVp (%) | 80 | 0 (0.0) | 0 (0.0) |
| | 100 | 34 (24.8) | 11 (11.0) |
| | 110 | 0 (0.0) | 0 (0.0) |
| | 120 | 86 (62.8) | 82 (82.0) |
| | 130 | 0 (0.0) | 1 (1.0) |
| | 140 | 17 (12.4) | 6 (6.0) |
| Slice | (median [IQR]) | 1.25 [1.25, 2.00] | 2.00 [1.25, 3.00] |
| Thickness | range | 0.625-3.0 | 0.625-4.0 |
| Pixel | (median [IQR]) | 0.78 [0.70, 0.87] | 0.81 [0.71, 0.98] |
| Spacing | range | 0.4316-0.9766 | 0.3711-1.6016 |

To capture quantitative data from the tumor microenvironment, a peripheral ring was created using 2 mm 3D dilation and erosion from the tumor boundaries, resulting in a 4 mm 3D ring. Large vessels, neighboring organs and air cavities were excluded if not invaded. Textural pattern can differ depending on tissue macrostructure. Thus, VOI locations were introduced as a parameter and labelled as "adenopathy" for node metastasis, "head and neck" for primary or secondary lesions of the pharynx, larynx, oral cavity or salivary glands, "lung" and "liver" for primary or secondary lesions of the lung or the liver respectively, and Length Matrix (GLRLM), the Neighborhood Gray-Level Difference Matrix (NGLDM) and the Gray-Level Zone Length Matrix (GLZLM). GLCM and GLRLM have been computed in 13 directions to account for all independent directions between one voxel and its 26 neighbors. Each textural feature extracted from these two matrices corresponds to the average value over the 13 directions.

Genomic Analysis for CD8 T-Cell Quantification

In the MOSCATO cohort, RNA-seq data were quantified using TPM (Transcript Per Million) method by the Salmon Tool© [43]. For the TCGA cohort, frozen RNA-seq data V4.6 of the TCGA Pan-cancer project [49] was used (https://www.synapse.org/#!Synapse:syn1701959). Data consisted of 20530 genes obtained with Illumina HiSeq RNASeqV2 (Illumina, San Diego, CA, USA) and quantified using RPKM (Reads Per Kilobase Million) method. All RNA-seq data were rescaled to have the same mean and variance as the training set, stratified by VOI location. For both cohorts, after log 2 transformation, abundance of CD8 T-cells was estimated using the gene expression signature based on the CD8B as defined by Becht et al. and the MCPcounter R-package [37] which also provided estimation of the absolute abundance of other tissue-infiltrating immune and stromal cell populations [37].

Variable Selection, Machine Learning

Input variables for the machine learning method consisted of 84 variables: 78 radiomic features, five locations (labeled as binary variables), and one global imaging variable, the peak kilovoltage (kVp), given its established impact on radiomic output [51]. A linear elastic-net model was used as regression method using the GLMNET R package version 2.0-10, for feature selection and model building [52]. The regularization parameter $\lambda$ was defined using cross-validation and the $\alpha$ penalty was set to 0.5 after a grid search. The machine learning algorithm—the radiomic-score—provides a mathematical formula that predicts the amount of CD8 T-cells estimated by the gene expression signature using imaging data, as follows:

$$\hat{y} = a_1 X_1 + a_2 X_2 + \ldots + a_i X_i + b$$

with:

$\hat{y}$=radiomic score $a_i$=coefficient of the variable i $X_i$=value of the variable i determined from the input image b=intercept A sensitivity analysis of the impact of the non-radiomic features on the signature's performance was done.

Pathologic Analysis

To assess the association between the radiomic-signature and pathologic analysis, histopathologic slides corresponding to primary tumors of patients in the TCGA dataset were retrieved from the Cancer Digital Slide Archive (http://cancer.digitalslidearchive.net/). Seventy-seven formalin-fixed paraffin-embedded tissues with hematoxylin and eosin stainings were available and analyzed by an independent pathologist, blinded to the radiomic results, to quantify the tumor-infiltrating lymphocytes (TIL) as a proportion of tumor area occupied by infiltrating lymphocytes (LIHC=10, HNSC=38, LUSC=12, LUAD=6, BLCA=11). No multiple imputation was made for the missing data.

Statistical Analysis

Wilcoxon signed-rank test or Kruskal-Wallis test for numerical variables, and Fisher test for categorical variables were considered. Area under the curve (AUC) of the receiver operator characteristic and its confidence interval according to the Delong method were computed to assess how the radiomic-signature score could separate patients into two groups depending on CD8 infiltration. These groups were defined according to the median value of CD8 T-cells gene expression in MOSCATO and TCGA datasets (primary endpoint), and as immune-desert or inflamed in the immune-phenotype dataset. Associations between the infiltrating CD8 T-cells, assessed either by gene expression or radiomics, with the other microenvironment cell populations estimated by gene expression signatures, were computed in TCGA and MOSCATO datasets ([37]). Correlations were assessed by Spearman's correlation coefficient.

In the IO-treated dataset, median value of the radiomic-score was used to cluster patients into high or low score. Follow-up and survival times were calculated from start of immunotherapy. Clinical responses were defined according to RECIST v1.1 as complete response (CR), partial response (PR), stable disease (SD), or progressive disease (PD), evaluated at 3 and 6 months. OS and PFS were computed according to the Kaplan-Meier method and Cox's proportional-hazards survival estimates. Endpoints were death from any cause for OS, and any recurrence or death for PFS. A multivariate analysis was performed and included the number of lines of treatment and the Royal Marsden Hospital prognostic score [53], since these were related to the OS in this cohort [50], and the tumor volume.

A threshold of <0.05 was defined for double-tailed P-value's significance. Statistical analyses were performed using R software version 3.4.1 (https://www.r-project.org/) ([45]).

Results

The MOSCATO training dataset used to build the radiomic-signature consisted of 135 patients included between May 1, 2012 to Mar. 31, 2016 (TABLE 12).

TABLE 12

| | Category | Overall |
|---|---|---|
| N patients | | 135 |
| Age (median [IQR]) | | 55.57 [41.39, 64.66] |
| Gender (%) | Female | 73 (54.1) |
| | Male | 62 (45.9) |
| Histology (%) | Adenoid Cystic carcinoma | 1 (0.7) |
| | Breast | 17 (12.6) |
| | Colorectal | 8 (5.9) |
| | Gynecological | 18 (13.3) |
| | Head and neck | 14 (10.4) |
| | Kidney | 1 (0.7) |
| | Liver | 9 (6.7) |
| | Lung | 30 (22.2) |
| | Neuroendocrine | 2 (1.5) |
| | Other* | 4 (3) |
| | Other epidermoid carcinoma** | 2 (1.5) |
| | Prostate | 7 (5.2) |
| | Sarcoma | 6 (4.4) |
| | Upper-GI | 8 (5.9) |
| | Urothelial | 8 (5.9) |
| VOI location (%) | Adenopathy | 22 (16.3) |
| | Liver | 54 (40.0) |
| | Head and Neck | 6 (4.4) |
| | Abdominopelvic or subcutaneous | 13 (9.6) |
| | Lung | 40 (29.6) |
| Genomic-based CD8 T-cells score (median [IQR]) | | 1.60 [0.89, 2.47] |

*Other: Spindle epithelial tumor with thymus-like differentiation (SETTLE), peritoneal desmoplastic small round cell tumor, hepatoblastoma, nephroblastoma

**Other epidermoid carcinoma: anal cancer, penile cancer

The TCGA validation dataset included 119 patients among the 435 patients available for screening at the time of inclusion (Jun. 30, 2017) (patient characteristics and flow-chart in Table 13).

TABLE 13

| | Category | Overall |
|---|---|---|
| N patients | | 119 |
| Age (median [IQR]) | | 61.00 [53.00, 70.00] |
| Gender (%) | Female | 34 (28.6) |
| | Male | 85 (71.4) |
| Cancer type (%) | Bladder | 11 (9.2) |
| | Head and neck | 76 (63.9) |
| | Hepatocellular carcinoma | 10 (8.4) |
| | Lung adenocarcinoma | 8 (6.7) |
| | Lung squamous cell carcinoma | 14 (11.8) |
| Genomic-based CD8 T-cells score (median [IQR]) | | 1.00 [0.52, 1.56] |

The "immune-phenotype dataset" consisted of 100 patients randomly selected from Aug. 24, 2005 to Nov. 19, 2015, with 70 (70%) tumors recognized to belong to the immune-inflamed group, and 30 (30%) tumors recognized to belong to the immune-desert group (Table 14).

TABLE 14

| | Category | Immune-desert | Inflamed |
|---|---|---|---|
| N patients | | 30 | 70 |
| Age (median [IQR]) | | 54.00 [46.00, 67.75] | 56.00 [38.50, 67.75] |

TABLE 14-continued

| | Category | Immune-desert | Inflamed |
|---|---|---|---|
| Gender (%) | Female | 20 (66.7) | 38 (54.3) |
| | Male | 10 (33.3) | 32 (45.7) |
| Histology (%) | Adenoid cystic carcinoma | 4 (13.3) | 0 (0.0) |
| | Colorectal | 2 (6.7) | 25 (35.7) |
| | Gynecological | 0 (0.0) | 1 (1.4) |
| | Kidney | 0 (0.0) | 3 (4.3) |
| | Leiomyoma | 7 (23.3) | 0 (0.0) |
| | Lung | 0 (0.0) | 6 (8.6) |
| | Lymphoma | 0 (0.0) | 25 (35.7) |
| | Melanoma | 0 (0.0) | 8 (11.4) |
| | Neuroendocrine | 17 (56.7) | 0 (0.0) |
| | Anal epidermoid carcinoma | 0 (0.0) | 1 (1.4) |
| | Urothelial | 0 (0.0) | 1 (1.4) |
| VOI location (%) | Adenopathy | 0 (0.0) | 39 (55.7) |
| | Liver | 10 (33.3) | 10 (14.3) |
| | Head and neck | 4 (13.3) | 0 (0.0) |
| | Abdominopelvic or subcutaneous | 8 (26.7) | 18 (25.7) |
| | Lung | 8 (26.7) | 3 (4.3) |
| MSI (%) | No | 30 (100.0) | 58 (82.9) |
| | Yes | 0 (0.0) | 12 (17.1) |
| Radiomic-score of CD8 T-cells (median [IQR]) | | 1.55 [1.50, 1.74] | 1.99 [1.59, 2.02] |

VOI: volume of interest, IQR: interquartile range, MSI: microsatellite instability

TABLE 15

| | Category | Overall | Radiomic-score of CD8 T-cells Low | High | P-value | Test |
|---|---|---|---|---|---|---|
| N patients | | 137 | 69 | 68 | | |
| Age (median [IQR]) | | 58.00 [45.00, 66.00] | 55.00 [42.00, 65.00] | 61.00 [48.50, 66.25] | 0.161 | Wilcoxon |
| Gender (%) | Female | 60 (43.8) | 29 (42.0) | 31 (45.6) | 0.732 | Fisher |
| | Male | 77 (56.2) | 40 (58.0) | 37 (54.4) | | |
| RMH Score (%) | 0 | 32 (23.4) | 15 (21.7) | 17 (25.0) | 0.930 | Fisher |
| | 1 | 48 (35.0) | 24 (34.8) | 24 (35.3) | | |
| | 2 | 47 (34.3) | 24 (34.8) | 23 (33.8) | | |
| | 3 | 10 (7.3) | 6 (8.7) | 4 (5.9) | | |
| Follow-up, months (median [IQR]) | | 16.53 [6.57, 38.90] | 10.58 [4.73, 26.05] | 23.51 [9.50, 44.51] | 0.002 | Wilcoxon |
| Number of lines before inclusion (median [IQR]) | | 2.00 [1.00, 4.00] | 2.00 [1.00, 3.00] | 2.00 [2.00, 4.00] | 0.118 | Wilcoxon |
| Histology (%) | Melanoma | 45 (32.8) | 23 (33.3) | 22 (32.4) | 0.298 | Fisher |
| | Lung | 17 (12.4) | 6 (8.7) | 11 (16.2) | | |
| | Urothelial | 12 (8.8) | 7 (10.1) | 5 (7.4) | | |
| | Kidney | 11 (8.0) | 5 (7.2) | 6 (8.8) | | |
| | Other | 11 (8.0) | 6 (8.7) | 5 (7.4) | | |
| | Gynecological | 9 (6.6) | 6 (8.7) | 3 (4.4) | | |
| | Liver | 8 (5.8) | 6 (8.7) | 2 (2.9) | | |
| | Lymphoma | 7 (5.1) | 1 (14) | 6 (8.8) | | |
| | Breast | 6 (4.4) | 2 (2.9) | 4 (5.9) | | |
| | Colorectal | 6 (4.4) | 5 (7.2) | 1 (15) | | |
| | Head neck | 5 (3.6) | 2 (2.9) | 3 (4.4) | | |
| VOI location (%) | Adenopathy | 53 (38.7) | 8 (11.6) | 45 (66.2) | <0.001 | Fisher |
| | Liver | 37 (27.0) | 37 (53.6) | 0 (0.0) | | |
| | Abdominopelvie or subcutaneous | 23 (16.8) | 20 (29.0) | 3 (4.4) | | |
| | Lung | 22 (16.1) | 2 (2.9) | 20 (29.4) | | |
| | Head and Neck | 2 (15) | 2 (2.9) | 0 (0.0) | | |
| Radiomic-score of CD8 T-cells (median [IQR]) | | 1.91 [1.67, 2.11] | 1.67 [1.63, 1.85] | 2.12 [2.06, 2.29] | <0.001 | Wilcoxon |

The IO-treated cohort consisted of 137 consecutive patients enrolled in anti-PD-1/PD-L1 phase 1 trials between Dec. 1, 2011 and Jan. 31, 2014 (TABLE 15).

VOI: volume of interest, IQR: interquartile range, RMH score: Royal Marsden Hospital prognostic score, other histologies: gastric or esophageal cancer (n=4), uveal melanoma (n=3), thyroid cancer (n=2), prostate cancer (n=1), sarcoma (n=1)

Development of a Radiomic Signature of CD8 T-Cells

The median genomic score of CD8 T-cells in the MOSCATO dataset was 1.60 (interquartile range IQR [0.89-2.47]). The score trained for the CD8 T-cells estimation using the elastic-net model (alpha=0.5, lambda=0.2) retained eight variables, including five radiomic features (one first-order and four second-order features from the Gray-Level Run Length Matrix), two VOI locations (adenopathy, head and neck), and the kVp variable (Table 16).

TABLE 16

| Features | Coefficient | P-values* |
|---|---|---|
| tum_minValue | −0.5133 | 0.00086 |
| tum_GLRLM_SRHGE | −0.1380 | 0.10 |
| ring_GLRLM_LGRE | 0.0839 | 0.10 |
| ring_GLRLM_SRLGE | 0.1049 | 0.044 |
| ring_GLRLM_LRLGE | 0.1216 | 0.013 |
| VOI_Adenopathy | 0.4286 | 0.020 |
| VOI_head_and_neck | −0.3673 | <0.0001 |
| kVp | −0.0109 | 0.44 |

Performance of the radiomic-signature to classify high versus low CD8 infiltrate was AUC=0.74, 95% CI [0.66-0.82], P-value<0.0001 in the training set (FIG. 6A). The radiomic-score of CD8 T-cells was not correlated with tumor volume (Spearman's rho=−0.10, P-value=0.26).

Validation of the Radiomic Signature

Performance of the radiomic-signature in the TCGA validation set was AUC=0.67, 95% CI [0.57-0.77], P-value=0.0019 (FIG. 6A). The radiomic-score was significantly higher in the immune-inflamed group than in the immune-desert: AUC=0.76, 95% CI [0.66-0.86], P-value<0.0001 (FIG. 6A) for the tumor immune-phenotype cohort. Data of sensitivity/specificity of this signature are presented on FIG. 9. For the IO-treated cohort, median follow-up [IQR] was 16.5 months [6.6-38.9]. At 3 months, the radiomic-score at baseline was higher in the 31 [22.6%] patients with objective response (CR+PR) compared to the 106 [77.4%] other patients (PD+SD) (P-value=0.049) but not significantly when considering the 63 (46.0%) patients with controlled disease (SD+CR+PR) vs the rest (PD: n=74 [54%] patients, P-value=0.050). At 6 months, it was significantly higher for both objective response and controlled disease (P-value=0.025 and P-value=0.013, respectively) (FIG. 6B, Table 17).

TABLE 17

| | Objective response N (%) | | | | Disease control N (%) | | |
|---|---|---|---|---|---|---|---|
| | PD + SD | CR + PR | P-value | | PD | SD + CR + PR | P-value |
| At 3 months | | | | | | | |
| N patients (%) Radiomics score: median + IQR | 106 (77.4) 1.89 (1.67-2.11) | 31 (22.6) 2.06 (1.85-2.13) | 0.049 | N patients (%) Radiomics score: median + IQR | 74 (54.0%) 1.88 (1.65-2.1) | 63 (46.0%) 1.97 (1.74-2.12) | 0.050 |
| At 6 months | | | | | | | |
| N patients (%) Radiomics score: median + IQR | 98 (71.5) 1.89 (1.66-2.11) | 39 (28.5) 2.06 (1.86-2.12) | 0.025 | N patients (%) Radiomics score: median + IQR | 82 (59.9) 1.88 (1.65-2.08) | 55 (40.1) 2.06 (1.8-2.13) | 0.013 |

Tum: radiomic feature from the tumor; Ring: radiomic feature from the peripheral ring around the tumor; VOI: location of the volume of interest; GLRLM: Gray-Level Run Length Matrix; SRHGE: short-run high gray-level emphasis; LGRE: low gray-level run emphasis; SRLGE: short-run low gray-level emphasis; LRLGE: long-run low gray-level emphasis; kVp: kilovoltage peak.

In the final score, the intercept value was of 3,413472.

*P-values of coefficients were computed after bootstrap method and presented for information purpose only. Given the nature of penalized regression, their interpretation should be made with caution since the estimation might not be as reliable as in the case of low dimensional linear regression.

PD: stable disease; DC: disease control; SD: stable disease; PR: partial response; CR: complete response OS was significantly higher in the high radiomic-score group (n=68 [49.6%] patients), HR=0.58, 95% CI [0.39-0.87], P-value=0.0081. Median OS was 24.3 months, 95% CI [18.63-42.1] vs. 11.5 months, 95% CI [7.98-15.6] in the low radiomic-score group (n=69 [50.4%] patients) (FIG. 6B).

This predictor appeared as the strongest independent prognostic factor in multivariate analysis (HR=0.52, 95% CI [0.35-0.79], P-value=0.0022) (Table 18).

TABLE 18

| | HR | CI 95% | P-value |
|---|---|---|---|
| Royal Marsden Hospital prognostic score ≥2 | 1.56 | 1.03-2.35 | 0.034 |
| Number of lines of treatment ≥2 | 2.05 | 1.27-3.31 | 0.0032 |

TABLE 18-continued

|  | HR | Cl 95% | P-value |
|---|---|---|---|
| Volume of the tumor | 1.00 | 1-1 | 0.19 |
| Radiomic-score of CD8 T-cells = High | 0.52 | 0.35-0.79 | 0.0022 |

Clinical Relevance of the Radiomic Signature

Correlations between signatures of CD8 T-cells (genomic- and radiomic-signatures) and other cell populations estimated by the MCP-counter gene signatures in the MOSCATO and TCGA cohorts were computed (Table 19).

TABLE 19

| Gene signature (MCP counter) | Gene signature | | Radiomic signature | |
|---|---|---|---|---|
|  | rho | p.adj | rho | p.adj |
| MOSCATO training dataset | | | | |
| REf: CD8 T cells | 1 | <1e−05 | 0.47 | <1e−05 |
| Cytotoxic lymphocytes | 0.64 | <1e−05 | 0.32 | 0.00037 |
| T cells | 0.65 | <1e−05 | 0.34 | 0.00025 |
| B lineage | 0.46 | <1e−05 | 0.48 | <1e−05 |
| NK cells | 0.48 | <1e−05 | 0.15 | 0.087 |
| Myeloid dendritic cells | 0.45 | <1e−05 | 0.18 | 0.057 |
| Endothelial cells | 0.29 | 9.00E−04 | 0.24 | 0.0088 |
| Monocytic lineage | 0.37 | 1.4e−05 | 0.16 | 0.078 |
| Fibroblasts | 0.25 | 0.0033 | 0.19 | 0.04 |
| Neutrophils | 0.00017 | 1 | −0.074 | 0.39 |
| TCGA training dataset | | | | |
| REf: CD8 T cells | 1 | <1e−05 | 0.41 | 1.9e−05 |
| Cytotoxic lymphocytes | 0.8 | <1e−05 | 0.23 | 0.03 |
| T cells | 0.77 | <1e−05 | 0.14 | 0.23 |
| B lineage | 0.68 | <1e−05 | 0.31 | 0.0023 |
| NK cells | 0.66 | <1e−05 | 0.1 | 0.4 |
| Myeloid dendritic cells | 0.57 | <1e−05 | 0.092 | 0.4 |
| Endothelial cells | 0.32 | 0.00044 | 0.16 | 0.18 |
| Monocytic lineage | 0.46 | <1e−05 | −0.017 | 0.86 |
| Fibroblasts | 0.11 | 0.23 | −0.059 | 0.59 |
| Neutrophils | −0.24 | 0.0088 | −0.47 | <1e−05 |

(Rho = Spearman's rho. P.adj = adjusted P-values according to Benjamini Hochberg method)

Significance was observed with most of the cell populations and genomic signature of CD8 T-cells, but higher one between the radiomic-score and T and B-cell lymphocyte gene-signatures for both sets. Significant negative correlations were seen between CD8 T-cells and tumor-associated neutrophils in the TCGA validation cohort with both genomic- and radiomic-signatures (P-value=0.0079 and <0.0001, respectively).

Correlations between the pathologist's quantification of TIL and the radiomic-score in the TCGA validation cohort was significant for the BLCA, LUAD, LUSC and LIHC subgroups (n=39/77 [50.6%]) (Spearman's rho=0.56, P-value=0.00022) (FIG. 7A), but not for the HNSC subgroup (n=38/77 [49.4%]) (P-value=0.18). We therefore conducted a post-hoc analysis pooling 93 head and neck tumors with different histologies (HNSC from MOSCATO (n=6 [6.5%] and TCGA (n=76 [81.7%]) ACC from the phenotype-based dataset (n=4 [4.3%]), and a sample of patients with undifferentiated nasopharyngeal cancers (UCNT) from our center (n=7 [7.5%]). The radiomic-predictor could significantly discriminate the different histologies in accordance with pathologically-assessed tumor immune infiltration such as ACC (lower infiltration than HNSCC), HNSCC and UCNT (higher infiltration) (FIG. 7B).

Discussion

This second signature comprises textural features from the GLRLM matrix ([47]). This matrix reflects homogeneity or heterogeneity of an image. An intuitive interpretation of the signature is that relatively homogeneous and hypodense tumors and peripheral rings were associated with a high CD8 T-cells score (see in [47] & [48]). These patterns could be representative of inflammatory infiltrate, while heterogeneity and high gray levels might be more representative of heterogeneous and intertwined processes like chaotic vascularization and necrosis.

It is notable that the signature included kVp and VOI locations. Retaining kVp highlights the need to account for image acquisition variability when cohorts are heterogenous, given that textural features are highly dependent on it [51, 57]. VOI locations were included by design to account for radiomic information likely related only to the organ analyzed since it is recognized that tissue origin exerts a major impact on the tumor immune contexture [58]. The machine learning model retained three groups: adenopathy, head and neck, and the rest. A sensitivity analysis was performed without the non-radiomic variables and showed poorer results, underscoring the importance of adjusting to these parameters when developing radiomics predictive tools (FIG. 8).

Interestingly, several points strengthening the biological and clinical relevance of this radiomic-signature have been identified. The abundance of CD8 T-cells (estimated either by the gene expression signature, or the radiomic-signature) was correlated with the abundance of other immune populations in both MOSCATO and TCGA datasets (especially the cytotoxic lymphocytes which encompass CD8 T-cells and NK cells, and the B lineage)(not shown). This correlation might be related to the presence of tertiary lymphoid structures (TLS) within the tumor; characterized by the association of T cells, mature DCs, a follicular center with follicular DCs, proliferating B cells, and high endothelial venules, and associated with favorable prognosis. Conversely, a negative correlation with tumor associated neutrophils (TANs) was found in the TCGA dataset. Yet, it has been shown that tumor cells can attract and activate immunosuppressive immune cells including TANs while blocking T-cell function. These correlations are then concordant with these biological processes. For clinical relevance, in the IO-treated cohort, while distribution of tumor types was not different between high and low radiomic-signature score groups, patients with liver lesions were in the low radiomic-score group corresponding to poor survival.

BIBLIOGRAPHIC REFERENCES

1. Limkin E J, Sun R, Dercle L et al. Promises and challenges for the implementation of computational medical imaging (radiomics) in oncology. Ann. Oncol. 2017; 28(6):1191-1206.
2. Aerts H J W L, Velazquez E R, Leijenaar R T H et al. Decoding tumour phenotype by noninvasive imaging using a quantitative radiomics approach. Nat. Commun. 2014; 5:4006.
3. Gillies R J, Kinahan P E, Hricak H. Radiomics: Images Are More than Pictures, They Are Data. Radiology 2016; 278(2):563-577.
4. O'Connor J P B, Rose C J, Waterton J C et al. Imaging intratumor heterogeneity: role in therapy response, resistance, and clinical outcome. Clin. Cancer Res. 2015; 21(2):249-257.
5. Reuze S, Orlhac F, Chargari C et al. Prediction of cervical cancer recurrence using textural features extracted from 18F-FDG PET images acquired with different scanners. Oncotarget 2017; 8(26):43169-43179.

6. Sun R, Orlhac F, Robert C et al. In Regard to Mattonen et al. Int. J. Radiat. Oncol. Biol. Phys. 2016; 95(5):1544-1545.

7. Robert C, Long G V, Brady B et al. Nivolumab in previously untreated melanoma without BRAF mutation. N. Engl. J. Med. 2015; 372(4):320-330.

8. Weber J S, Kudchadkar R R, Yu B et al. Safety, efficacy, and biomarkers of nivolumab with vaccine in ipilimumab-refractory or -naive melanoma. J. Clin. Oncol. 2013; 31(34):4311-4318.

9. Ansell S M. Hodgkin Lymphoma: Diagnosis and Treatment. Mayo Clin. Proc. 2015; 90(11):1574-1583.

10. Reck M, Rodriguez-Abreu D, Robinson A G et al. Pembrolizumab versus Chemotherapy for PD-L1-Positive Non-Small-Cell Lung Cancer. N. Engl. J. Med. 2016; 375(19):1823-1833.

11. Motzer R J, Escudier B, McDermott D F et al. Nivolumab versus Everolimus in Advanced Renal-Cell Carcinoma. N. Engl. J. Med. 2015; 373(19):1803-1813.

12. Chen D S, Mellman I. Elements of cancer immunity and the cancer-immune set point. Nature 2017; 541(7637):321-330.

13. Postow M A, Chesney J, Pavlick A C et al. Nivolumab and ipilimumab versus ipilimumab in untreated melanoma. N. Engl. J. Med. 2015; 372(21):2006-2017.

14. Hellmann M D, Rizvi N A, Goldman J W et al. Nivolumab plus ipilimumab as first-line treatment for advanced non-small-cell lung cancer (CheckMate 012): results of an open-label, phase 1, multicohort study. Lancet Oncol. 2017; 18(1):31-41.

15. Herbst R S, Soria J-C, Kowanetz M et al. Predictive correlates of response to the anti-PD-L1 antibody MPDL3280A in cancer patients. Nature 2014; 515(7528):563-567.

16. Kim J M, Chen D S. Immune escape to PD-L1/PD-1 blockade: seven steps to success (or failure). Ann. Oncol. 2016; 27(8):1492-1504.

17. Hugo W, Zaretsky J M, Sun L et al. Genomic and Transcriptomic Features of Response to Anti-PD-1 Therapy in Metastatic Melanoma. Cell 2016; 165(1):35-44.

18. Ribas A, Shin D S, Zaretsky J et al. PD-1 Blockade Expands Intratumoral Memory T Cells. Cancer Immunol Res 2016; 4(3)194-203.

19. Tumeh P C, Harview C L, Yearley J H et al. PD-1 blockade induces responses by inhibiting adaptive immune resistance. Nature 2014; 515(7528):568-571.

20. Rosenberg J E, Hoffman-Censits J, Powles T et al. Atezolizumab in patients with locally advanced and metastatic urothelial carcinoma who have progressed following treatment with platinum-based chemotherapy: a single-arm, multicentre, phase 2 trial. Lancet 2016; 387 (10031):1909-1920.

21. Clemente C G, Mihm M C Jr, Bufalino R et al. Prognostic value of tumor infiltrating lymphocytes in the vertical growth phase of primary cutaneous melanoma. Cancer 1996; 77(7):1303-1310.

22. Sato E, Olson S H, Ahn J et al. Intraepithelial CD8+ tumor-infiltrating lymphocytes and a high CD8+/regulatory T cell ratio are associated with favorable prognosis in ovarian cancer. Proc. Natl. Acad. Sci. U.S.A. 2005; 102 (51)18538-18543.

23. Pages F, Berger A, Camus M et al. Effector memory T cells, early metastasis, and survival in colorectal cancer. N. Engl. J. Med. 2005; 353(25):2654-2666.

24. Ogino T, Shigyo H, Ishii H et al. HLA class I antigen down-regulation in primary laryngeal squamous cell carcinoma lesions as a poor prognostic marker. Cancer Res. 2006; 66(18):9281-9289.

25. Balermpas P, Michel Y, Wagenblast J et al. Tumour-infiltrating lymphocytes predict response to definitive chemoradiotherapy in head and neck cancer. Br. J. Cancer 2014; 110(2):501-509.

26. Wansom D, Light E, Thomas D et al. Infiltrating lymphocytes and human papillomavirus-16-associated oropharyngeal cancer. Laryngoscope 2012; 122(1):121-127.

27. Melero I, Rouzaut A, Motz G T, Coukos G. T-cell and NK-cell infiltration into solid tumors: a key limiting factor for efficacious cancer immunotherapy. Cancer Discov. 2014; 4(5):522-526.

28. Joyce J A, Fearon D T. T cell exclusion, immune privilege, and the tumor microenvironment. Science 2015; 348(6230):74-80.

29. Salmon H, Franciszkiewicz K, Damotte D et al. Matrix architecture defines the preferential localization and migration of T cells into the stroma of human lung tumors. J. Clin. Invest. 2012; 122(3):899-910.

30. Gajewski T F, Woo S-R, Zha Y et al. Cancer immunotherapy strategies based on overcoming barriers within the tumor microenvironment. Curr. Opin. Immunol. 2013; 25(2):268-276.

31. Hegde P S, Karanikas V, Evers S. The Where, the When, and the How of Immune Monitoring for Cancer Immunotherapies in the Era of Checkpoint Inhibition. Clin. Cancer Res. 2016; 22(8):1865-1874.

32. Orooji M, Rakshit S, Beig N et al. Computerized textural analysis of lung CT to enable quantification of tumor infiltrating lymphocytes in NSCLC. J. Clin. Oncol. 2016; 34(15_suppl):11584-11584.

33. Tang C, Amer A, Hobbs B et al. Pathology-Based Non-Small Cell Lung Cancer Radiomics Signature Describing the Local Tumor Immune Environment: Discovery and Validation. Int. J. Radiat. Oncol. Biol. Phys. 2016; 96(2):542-543.

34. Prawira A, Dufort P, Halankar J et al. Development of a predictive radiomics signature for response to immune checkpoint inhibitors (ICIs) in patients with recurrent or metastatic squamous cell carcinoma of the head and neck (RM-SCCHN). Ann. Oncol. 2016. doi:10.1093/annonc/mdw376.08.

35. Website. [Zuley, M. L., Jarosz, R., Kirk, S., Lee, Y., Colen, R., Garcia, K., . . . Aredes, N. D. (2016). Radiology Data from The Cancer Genome Atlas Head-Neck Squamous Cell Carcinoma [TCGA-HNSC] collection. The Cancer Imaging Archive. http://doi.org/10.7937/K9/TCIA.2016. LXKQ47MS].

36. Clark K, Vendt B, Smith K et al. The Cancer Imaging Archive (TCIA): maintaining and operating a public information repository. J. Digit. Imaging 2013; 26(6): 1045-1057.

37. Becht E, Giraldo N A, Lacroix L et al. Estimating the population abundance of tissue-infiltrating immune and stromal cell populations using gene expression. Genome Biol. 2016; 17(1):218.

38. Nioche C, Orlhac F, Boughdad S et al. A freeware for tumor heterogeneity characterization in PET, SPECT, CT, MRI and US to accelerate advances in radiomics. J Nucl Med 2017; 58(supplement 1):1316-1316.

39. Leijenaar R T H, Nalbantov G, Carvalho S et al. The effect of SUV discretization in quantitative FDG-PET Radiomics: the need for standardized methodology in tumor texture analysis. Sci. Rep. 2015; 5:11075.

40. Kuhn M, Wing J, Weston S et al. caret: Classification and Regression Training, 2017.

41. Liaw A, Wiener M. Classification and Regression by randomForest. R News 2002; 2(3):18-22.

42. Massard C, Michiels S, Ferte C et al. High-Throughput Genomics and Clinical Outcome in Hard-to-Treat Advanced Cancers: Results of the MOSCATO 01 Trial. Cancer Discov. 2017; 7(6):586-595.

43. Nioche C, Orlhac F, Boughdad S, Reuze S, Goya-Outi J, Robert C, Pellot-Barakat, C, Soussan M, Frouin F, Buvat I. LIFEx: a freeware for radiomic feature calculation in multimodality imaging to accelerate advances in the characterization of tumor heterogeneity. Cancer Res. 2018 Jun. 29.

44. Champiat S, Dercle L, Ammari S et al. Hyperprogressive Disease Is a New Pattern of Progression in Cancer Patients Treated by Anti-PD-1/PD-L1. Clin. Cancer Res. 2017; 23(8):1920-1928.

45. R Core Team. R: A Language and Environment for Statistical Computing, R Foundation for Statistical Computing, Vienna, Austria, 2017.

46. Cataldo S D, Ficarra E. Mining textural knowledge in biological images: applications, methods and trends. Comput Struct Biotechnol J 2016

47. Galloway M M. Texture analysis using gray level run lengths. *Computer Graphics and Image Processing* 1975; 4: 172-9.

48. Orlhac F, Nioche C, Soussan M, Buvat I. Understanding Changes in Tumor Texture Indices in PET: A Comparison Between Visual Assessment and Index Values in Simulated and Patient Data. *J Nucl Med* 2017; 58: 387-92.

49 Cancer Genome Atlas Research Network, Weinstein J N, Collisson E A, et al. The Cancer Genome Atlas Pan-Cancer analysis project. Nat Genet 2013; 45: 1113-20.

50 Sun R, Champiat S, Dercle L, et al. Baseline lymphopenia should not be used as exclusion criteria in early clinical trials investigating immune checkpoint blockers (PD-1/PD-L1 inhibitors). Eur J Cancer 2017; 84: 202-11.

51 Miles K A, Ganeshan B, Griffiths M R, Young R C D, Chatwin C R. Colorectal cancer: texture analysis of portal phase hepatic CT images as a potential marker of survival. Radiology 2009; 250: 444-52.

52 Zou H, Hastie T. Regularization and variable selection via the elastic net. J R Stat Soc Series B Stat Methodol 2005; 67: 301-20.

53 Arkenau H-T, Barriuso J, Olmos D, et al. Prospective validation of a prognostic score to improve patient selection for oncology phase I trials. J Clin Oncol 2009; 27: 2692-6.

54 Braman N M, Etesami M, Prasanna P, et al. Intratumoral and peritumoral radiomics for the pretreatment prediction of pathological complete response to neoadjuvant chemotherapy based on breast DCE-MRI. Breast Cancer Res 2017; 19: 57.

55 Gandhi L, Rodriguez-Abreu D, Gadgeel S, et al. Pembrolizumab plus Chemotherapy in Metastatic Non-Small-Cell Lung Cancer. N Engl J Med 2018; published online April 16. DOI:10.1056/NEJMoa1801005.

56 Antonia S J, Villegas A, Daniel D, et al. Durvalumab after Chemoradiotherapy in Stage III Non-Small-Cell Lung Cancer. N Engl J Med 2017; 377: 1919-29.

57 Fletcher J G, Leng S, Yu L, McCollough C H. Dealing with Uncertainty in CT Images. Radiology 2016; 279: 5-10.

58 Pao W, Ooi C-H, Birzele F, et al. Tissue-Specific Immunoregulation: A Call for Better Understanding of the 'Immunostat' in the Context of Cancer. Cancer Discov 2018; 8: 395-402.

59 Tang C, Hobbs B, Amer A, et al. Development of an Immune-Pathology Informed Radiomics Model for Non-Small Cell Lung Cancer. Sci Rep 2018; 8: 1922.

60 Grossmann P, Stringfield O, El-Hachem N, et al. Defining the biological basis of radiomic phenotypes in lung cancer. Elife 2017; 6. DOI:10.7554/eLife.23421.

61 Chen R-Y, Lin Y-C, Shen W-C, et al. Associations of Tumor PD-1 Ligands, Immunohistochemical Studies, and Textural Features in18F-FDG PET in Squamous Cell Carcinoma of the Head and Neck. Sci Rep 2018; 8: 105.

62 Eisenhauera E A, Therasseb P, Bogaertsc J, et al. New response evaluation criteria in solid tumours: Revised RECIST guideline (version 1.1). EurJ Cancer 2009, 45: 228-247

The invention claimed is:

1. A method for evaluating the spatial density of a CD8+ T cells infiltrate in a solid tumor, said method comprising:
   a) specifying two regions of interest (ROI) in a radiological image of a region of a tumoral tissue of a solid tumor, said radiological image including a plurality of voxels, wherein the two ROI are:
      a solid tumor volume and
      a peripheral ring volume created around the solid tumor margin;
   b) extracting a set of features from said two ROI, wherein the set of features comprises:
      Min Value of the tumor as conventional variable,
      at least three Gray-level Run Length Matrix (GLRLM) variables selected from:
         GLRLM short-run high gray-level emphasis (GLRLM_SRHGE) of the solid tumor,
         GLRLM short-run low gray-level emphasis (GLRLM_SRLGE) of the peripheral ring volume,
         GLRLM low gray-level run emphasis (GLRLM_LGRE) of the peripheral ring volume, and
         GLRLM long-run low gray-level emphasis (GLRLM_LRLGE) of the peripheral ring volume;
      acquisition marker kilovoltage peak (kVp), and
      location of adenopathy (VOI_Adenopathy) and location of head and neck cancer (VOI_head_and_neck), wherein the values of VOI Adenopathy and VOI head and neck are null when the target tumors are not from adenopathy or head-and-neck; and
   c) providing the extracted features to a trained machine learning predictor which calculates a quantitative score of the spatial density of the CD8+ T cells infiltrate in the solid tumor.

2. The method of claim 1, wherein said radiological image is generated using non-invasive imaging technologies.

3. The method of claim 1, wherein said radiological image is generated using scanners, magnetic resonance imaging (MRI), or PET (Positron Emission Tomography).

4. The method of claim 1, wherein said radiological image is generated using a computed tomography (CT) scan.

5. The method of claim 1, wherein said set of features comprises:
   GLRLM short-run high gray-level emphasis (GLRLM_SRHGE) of the tumor,
   GLRLM short-run low gray-level emphasis (GLRLM_SRLGE) of the ring,
   GLRLM low gray-level run emphasis (GLRLM_LGRE) of the ring, and GLRLM long-run low gray-level emphasis (GLRLM_LRLGE) of the ring.

6. The method of claim 1, wherein said solid tumor is squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, brain cancer, central nervous system cancer, pancreatic cancer, glioblastoma multiforme, cervical cancer, stomach cancer, bladder cancer, malignant hepatoma, breast cancer, colon carcinoma, head and neck cancer, gastric cancer, germ cell tumor, pediatric sarcoma, rhabdomyosarcoma, Ewing's sarcoma, osteosarcoma, soft tissue sarcoma, sinonasal NK/T-cell lymphoma, myeloma, melanoma, multiple myeloma, or benign solid tumors such as uterine leiomyosarcoma.

7. The method of claim 1, wherein said set of features consists essentially of said MinValue, at least three GLRLM variables, kVp, and said VOI_Adenopathy and VOI-_head_and_neck variables, wherein the values of VOI Adenopathy and VOI head and neck are null when the target tumors are not from adenopathy or head-and-neck.

8. A method for predicting the outcome or the efficiency of an anti-cancer treatment for a cancer patient with a tumor, said method comprising:
   a) specifying two regions of interest (ROI) in a radiological image of a region of a tumoral tissue of a solid tumor, said radiological image including a plurality of voxels, wherein the two ROI are:
      a solid tumor volume and
      a peripheral ring volume created around the solid tumor margin;
   b) extracting a set of features from said two ROI, wherein the set of features comprises:
      Min Value of the tumor as conventional variable,
      at least three Gray-level Run Length Matrix (GLRLM) variables selected from
         GLRLM short-run high gray-level emphasis (GLRLM_SRHGE) of the solid tumor,
         GLRLM short-run low gray-level emphasis (GLRLM_SRLGE) of the peripheral ring volume,
         GLRLM low gray-level run emphasis (GLRLM_L-GRE) of the peripheral ring volume, and GLRLM long-run low gray-level emphasis (GLRLM_LRLGE) of the peripheral ring volume;
      acquisition marker kilovoltage peak (kVp), and
      location of adenopathy (VOI_Adenopathy) and location of head and neck cancer (VOI_head_and_neck), wherein the values of VOI Adenopathy and VOI head and neck are null when the target tumors are not from adenopathy or head-and-neck; and
   c) providing the extracted features to a trained machine learning predictor which calculates a quantitative score of the spatial density of the CD8+ T cells infiltrate in the solid tumor.

9. The method of claim 8, wherein said anti-cancer treatment is a chemotherapeutic treatment, an immunotherapeutic treatment, a radiotherapeutic treatment, and/or surgery.

10. The method of claim 8, wherein said anti-cancer treatment is an immunotherapeutic treatment with anti-PD-1 and/or anti-PD-L1 drugs.

11. The method of claim 8, wherein said radiological image is generated using a CT scan.

12. The method of claim 8, wherein said set of features comprises:
   GLRLM short-run high gray-level emphasis (GLRLM_SRHGE) of the solid tumor,
   GLRLM short-run low gray-level emphasis (GLRLM_SRLGE) of the peripheral ring volume,
   GLRLM low gray-level run emphasis (GLRLM_LGRE) of the peripheral ring volume, and
   GLRLM long-run low gray-level emphasis (GLRLM_LRLGE) of the peripheral ring volume.

13. The method of claim 8, wherein said set of features consists essentially of said MinValue, at least three GLRLM variables, kVp, and said VOI_Adenopathy and VOI-_head_and_neck variables, wherein the values of VOI Adenopathy and VOI head and neck are null when the target tumors are not from adenopathy or head-and-neck.

14. The method of claim 8, wherein said method is for assessing progression-free survival (PFS) or overall survival (OS) of the cancer patient.

* * * * *